US007700773B2

(12) United States Patent
Mallams et al.

(10) Patent No.: US 7,700,773 B2
(45) Date of Patent: Apr. 20, 2010

(54) 4-CYANO, 4-AMINO, AND 4-AMINOMETHYL DERIVATIVES OF PYRAZOLO[1,5-A]PYRIDINES, PYRAZOLO[1,5-C]PYRIMIDINES AND 2H-INDAZOLE COMPOUNDS AND 5-CYANO, 5-AMINO, AND 5-AMINOMETHYL DERIVATIVES OF IMIDAZO[1,2-A]PYRIDINES, AND IMIDAZO[1,5-A]PYRAZINES AS CYCLIN DEPENDENT KINASE INHIBITORS

(75) Inventors: Alan K. Mallams, Hackettstown, NJ (US); Vincent S. Madison, Moutain Lakes, NJ (US); Kamil Paruch, Garwood, NJ (US)

(73) Assignee: Schering Corporation, Kenilworth, NJ (US)

( * ) Notice: Subject to any disclaimer, the term of this patent is extended or adjusted under 35 U.S.C. 154(b) by 286 days.

(21) Appl. No.: 11/514,548

(22) Filed: Aug. 31, 2006

(65) Prior Publication Data

US 2007/0066621 A1 Mar. 22, 2007

Related U.S. Application Data

(60) Provisional application No. 60/715,621, filed on Sep. 9, 2005.

(51) Int. Cl.
C07D 491/02 (2006.01)
C07D 498/02 (2006.01)
(52) U.S. Cl. .................................................... 546/121
(58) Field of Classification Search .................. 546/121
See application file for complete search history.

(56) References Cited

U.S. PATENT DOCUMENTS

| 5,571,813 | A | 11/1996 | Rühter et al. |
| 5,602,136 | A | 2/1997 | Rühter et al. |
| 5,602,137 | A | 2/1997 | Rühter et al. |
| 5,688,949 | A | 11/1997 | Inoue et al. |
| 5,707,997 | A | 1/1998 | Shoji et al. |
| 6,107,305 | A | 8/2000 | Misra et al. |
| 6,383,790 | B1 | 5/2002 | Shokat |
| 6,413,974 | B1 | 7/2002 | Dumont et al. |
| 6,897,208 | B2 | 5/2005 | Edwards et al. |
| 6,949,579 | B2 | 9/2005 | Dutruc-Rosset et al. |
| 7,067,520 | B2 | 6/2006 | Kato et al. |
| 7,417,053 | B2 * | 8/2008 | Unoki et al. ............... 514/300 |
| 2002/0173445 | A1 * | 11/2002 | Salvati et al. ............... 514/1 |
| 2004/0048849 | A1 | 3/2004 | Prevost et al. |
| 2004/0063715 | A1 | 4/2004 | Paruch et al. |
| 2004/0067951 | A1 | 4/2004 | DeSimone et al. |
| 2004/0072835 | A1 | 4/2004 | Paruch et al. |
| 2004/0102452 | A1 | 5/2004 | Guzi et al. |

FOREIGN PATENT DOCUMENTS

| EP | 0 628 559 B1 | 4/2002 |
| FR | 2 836 915 A1 | 9/2003 |
| WO | WO 95/35298 A1 | 12/1995 |
| WO | WO 02/10162 A1 | 2/2002 |
| WO | WO 02/40485 A1 | 5/2002 |
| WO | WO 02/50079 A1 | 6/2002 |
| WO | WO 92/18504 A1 | 10/2002 |
| WO | 03062241 * | 7/2003 |
| WO | WO 2004/014864 A1 | 2/2004 |
| WO | WO 2004/022062 A1 | 3/2004 |
| WO | WO 2004/022559 A1 | 3/2004 |
| WO | WO 2004/022560 A1 | 3/2004 |
| WO | WO 2004/022561 A1 | 3/2004 |
| WO | WO 2004/026229 A2 | 4/2004 |
| WO | WO 2004/026310 A1 | 4/2004 |
| WO | WO 2004/026867 A2 | 4/2004 |
| WO | WO 2004/026872 A1 | 4/2004 |
| WO | WO 2004/026877 A | 4/2004 |

OTHER PUBLICATIONS

Senderowicz et al., "Phase I Trial of Continuous Infusion Flavopiridol, a Novel Cyclin-Dependent Kinase Inhibitor, in Patients with Refractory Neoplasms", Journal of Clinical Oncology, 16(9): 2986-2999 (Sep. 1998).
Vesely et al., "Inhibition of Cyclin-Dependent Kinases by Purine Analogues", Eur. J. Biochem, 224: 771-786 (1994).
Meijer et al., "Biochemical and Cellular Effects of Roscovitine, a Potent and Selective Inhibitor of the Cyclin-Dependent Kinases CDC2, CDK2 and CDK5", Eur. J. Biochem , 243:527-536 (1997).
Kim et al., "Discovery of Aminothiazole Inhibitors of Cyclin-Dependent Kinase 2: Synthesis, X-ray Crystallographic Analysis, and Biological Activities", Journal of Medicinal Chemistry, 45:3905-3927 (2002).
Novinson et al., "Synthesis and Antifungal Properties of Certain 7-Alkylaminopyrazolo[1,5-a]pyrimidines", Journal of Medicinal Chemistry, 20(2): 296-299 (1977).
Novinson et al., "Synthesis and Antimicrobial Activity of Some Novel Heterocycles. Azolo-as-Triazines", Journal of Medicinal Chemistry, 19(4): 517-520 (2003).
Annex to Form PCT/ISA/206 Communication Relating to the results of the partial International Search dated Jan. 4, 2007 for corresponding International Application PCT/US2006/034233.

* cited by examiner

Primary Examiner—D. Margaret Seaman
Assistant Examiner—Niloofar Rahmani
(74) Attorney, Agent, or Firm—Serena Farquharson-Torres

(57) ABSTRACT

In its many embodiments, the present invention provides a novel class of 4-cyano, 4-amino, and 4-aminomethyl derivatives of pyrazolo[1,5-a]pyridine, pyrazolo[1,5-c]pyrimidine, and 2H-Indazole compounds and 5-cyano, 5-amino, and 5-aminomethyl derivatives of imidazo[1,2-a]pyridine and imidazo[1,5-a]pyrazine compounds as inhibitors of cyclin dependent kinases, methods of preparing such compounds, pharmaceutical compositions containing one or more such compounds, methods of preparing pharmaceutical formulations comprising one or more such compounds, and methods of treatment, prevention, inhibition, or amelioration of one or more diseases associated with the CDKs using such compounds or pharmaceutical compositions.

20 Claims, No Drawings

4-CYANO, 4-AMINO, AND 4-AMINOMETHYL DERIVATIVES OF PYRAZOLO[1,5-A]PYRIDINES, PYRAZOLO[1,5-C]PYRIMIDINES AND 2H-INDAZOLE COMPOUNDS AND 5-CYANO, 5-AMINO, AND 5-AMINOMETHYL DERIVATIVES OF IMIDAZO[1,2-A]PYRIDINES, AND IMIDAZO[1,5-A]PYRAZINES AS CYCLIN DEPENDENT KINASE INHIBITORS

RELATED APPLICATION

This application claims priority to provisional application U.S. Ser. No. 60/715,621 filed on Sep. 9, 2005, herein incorporated by reference.

FIELD OF THE INVENTION

The present invention relates to 4-cyano, 4-amino, and 4-aminomethyl derivatives of pyrazolo[1,5-a]pyridine, pyrazolo[1,5-c]pyrimidine, and 2H-Indazole compounds and 5-cyano, 5-amino, and 5-aminomethyl derivatives of imidazo[1,2-a]pyridine and imidazo[1,5-a]pyrazine compounds useful as protein kinase inhibitors, pharmaceutical compositions containing the compounds, and methods of treatment using the compounds and compositions to treat diseases such as, for example, cancer, inflammation, arthritis, viral diseases, neurodegenerative diseases such as Alzheimer's disease, cardiovascular diseases, and fungal diseases.

BACKGROUND OF THE INVENTION

The cyclin-dependent kinases (CDKs) are serine/threonine protein kinases, which are the driving force behind the cell cycle and cell proliferation. Individual CDK's, such as, CDK1, CDK2, CDK3, CDK4, CDK5, CDK6 and CDK7, CDK8 and the like, perform distinct roles in cell cycle progression and can be classified as either G1, S, or G2M phase enzymes. Uncontrolled proliferation is a hallmark of cancer cells, and misregulation of CDK function occurs with high frequency in many important solid tumors. CDK2 and CDK4 are of particular interest because their activities are frequently misregulated in a wide variety of human cancers. CDK2 activity is required for progression through G1 to the S phase of the cell cycle, and CDK2 is one of the key components of the G1 checkpoint. Checkpoints serve to maintain the proper sequence of cell cycle events and allow the cell to respond to insults or to proliferative signals, while the loss of proper checkpoint control in cancer cells contributes to tumorgenesis. The CDK2 pathway influences tumorgenesis at the level of tumor suppressor function (e.g. p52, RB, and p27) and oncogene activation (cyclin E). Many reports have demonstrated that both the coactivator, cyclin E, and the inhibitor, p27, of CDK2 are either over—or underexpressed, respectively, in breast, colon, nonsmall cell lung, gastric, prostate, bladder, non-Hodgkin's lymphoma, ovarian, and other cancers. Their altered expression has been shown to correlate with increased CDK2 activity levels and poor overall survival. This observation makes CDK2 and its regulatory pathways compelling targets for the development years, a number of adenosine 5'-triphosphate (ATP) competitive small organic molecules as well as peptides have been reported in the literature as CDK inhibitors for the potential treatment of cancers. U.S. Pat. No. 6,413,974, col. 1, line 23—col. 15, line 10 offers a good description of the various CDKs and their relationship to various types of cancer.

CDK inhibitors are known. For example, flavopiridol (Formula I) is a nonselective CDK inhibitor that is currently undergoing human clinical trials, A. M. Sanderowicz et al, *J. Clin. Oncol.* (1998) 16, 2986-2999.

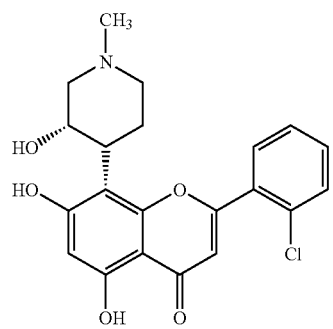

Formula I

Other known inhibitors of the CDKs include, for example, olomoucine (J. Vesely et al, *Eur. J. Biochem.*, (1994) 224, 771-786) and roscovitine (I. Meijer et al, *Eur. J. Biochem.*, (1997) 243, 527-536). U.S. Pat. No. 6,107,305 describes certain pyrazolo[3,4-b] pyridine compounds as CDK inhibitors. An illustrative compound from the '305 patent has the Formula II:

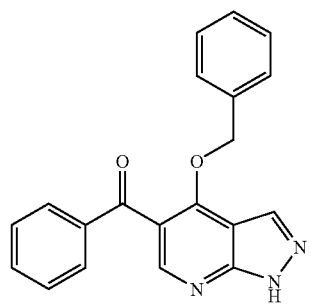

Formula II

K. S. Kim et al, *J. Med. Chem.* 45 (2002) 3905-3927 and WO 02/10162 disclose certain aminothiazole compounds as CDK inhibitors.

Pyrazolopyrimidines are known. For Example, WO92/18504, WO02/50079, WO95/35298, WO02/40485, EP94304104.6, EP0628559, (equivalent to U.S. Pat. Nos. 5,602,136, 5,602,137 and 5,571,813), U.S. Pat. No. 6,383,790, WO04/022561, WO04/026229, WO04/022559, WO04/022062, WO04/022560, *Chem. Pharm. Bull.*, (1999) 47 928, *J. Med. Chem.*, (1977) 20, 296, *J. Med. Chem.*, (1976) 19 517 and *Chem. Pharm. Bull.*, (1962) 10 620 disclose various pyrazolopyrimidines.

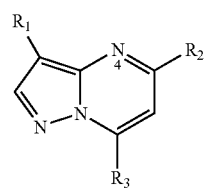

Pyrazolo[1,5-a]pyrimidines

Imidazopyrazines are also known. For Example, WO04/026877 and WO04/026310 disclose various imidazopyrazines

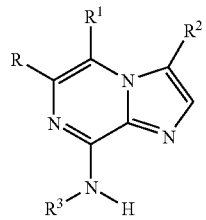

wherein: R¹ is H, halogen, or alkyl.

Additionally, Imidazopyridines and pyrazolopyridines are known. For Example, WO04/026867 discloses various imidazopyridines and WO04/026872 discloses various pyrazolopyridines

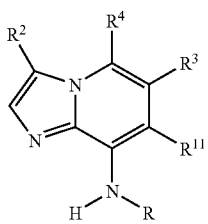

Imidazopyridine

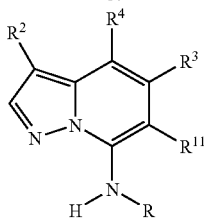

pyrazolopyridine wherein R⁴ does not include a cyano or amino substituent.

Benzimidazoles are known. For example, U.S. Pat. No. 6,897,208 discloses various benzimidazoles.

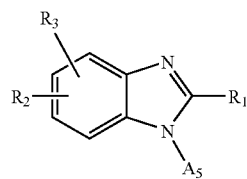

There is a need for new compounds, formulations, treatments and therapies to treat diseases and disorders associated with CDKs. It is, therefore, an object of this invention to provide compounds useful in the treatment or prevention or amelioration of such diseases and disorders.

SUMMARY OF THE INVENTION

In its many embodiments, the present invention provides a novel class of 4-cyano, 4-amino, and 4-aminomethyl derivatives of pyrazolo[1,5-a]pyridine, pyrazolo[1,5-c]pyrimidine, and 2H-Indazole compounds and 5-cyano, 5-amino, and 5-aminomethyl derivatives of imidazo[1,2-a]pyridine and imidazo[1,5-a]pyrazine compounds as inhibitors of cyclin dependent kinases, methods of preparing such compounds, pharmaceutical compositions comprising one or more such compounds, methods of preparing pharmaceutical formulations comprising one or more such compounds, and methods of treatment, prevention, inhibition or amelioration of one or more diseases associated with the CDKs using such compounds or pharmaceutical compositions.

In one aspect, the present application discloses a compound, or pharmaceutically acceptable salts or solvates of said compound, said compound having the general structure shown in anyone of Formulas III-VII:

Formula III

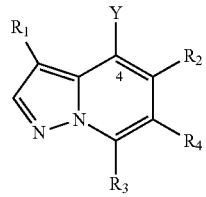

Formula V

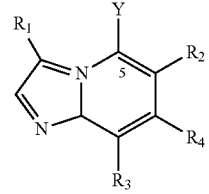

Formula VII

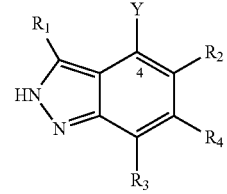

Formula IV

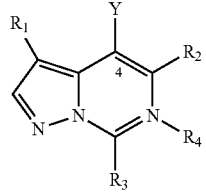

Formula VI

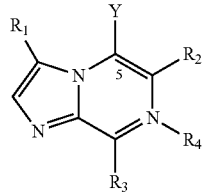

wherein:

Y is selected from the group consisting of CN, $NH_2$, and $CH_2NH_2$;

$R^1$ is selected from the group consisting of H, halogen, $R^9$, $NH_2$, CN, alkyl, alkenyl, alkynyl, aryl, heteroaryl, $CF_3$, heterocyclylalkyl, arylalkyl, heteroarylalkyl, heterocycloalkylalkyl, cycloalkyl, cycloalkylalkyl, $C(O)OR^4$, alkyl substituted with 1-6 $R^9$ groups which can be the same or different and are independently selected from the list of $R^9$ shown later below,

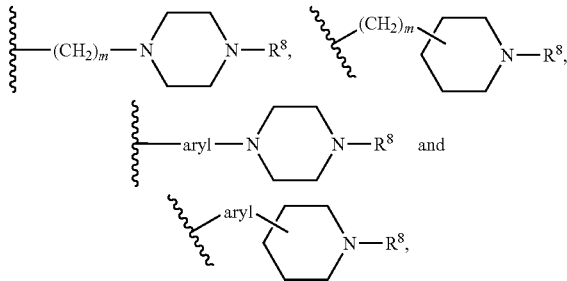

wherein the aryl in the above-noted definitions for $R^1$ can be unsubstituted or optionally substituted with one or more moieties which can be the same or different, each moiety being independently selected from the group consisting of halogen, CN, $NH_2$, —$OR^5$, $SR^5$, —$CH_2OR^5$, —$C(O)R^5$, —$SO_3H$, —$S(O_2)R^6$, —$S(O_2)NR^5R^6$, —$NR^5R^6$, —$C(O)NR^5R^6$, —$CF_3$, and —$OCF_3$;

$R^2$ is selected from the group consisting of H, halogen, —$NR^5R^6$, —$C(O)OR^4$, —$C(O)NR^5R^6$, alkyl, alkenyl, alkynyl, cycloalkyl, cycloalkylalkyl, aryl, arylalkyl, heterocyclyl, heterocyclylalkyl, heteroaryl,

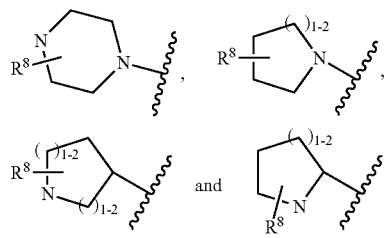

wherein each of said alkyl, alkenyl, alkynyl, cycloalkyl, aryl, arylalkyl, heterocyclylalkyl, heteroaryl and heteroarylalkyl for $R^2$ and heterocyclyl moieties whose structures are shown immediately above for $R^2$ can be unsubstituted or optionally independently substituted with one or more moieties which can be the same or different, each moiety being independently selected from the group consisting of halogen, alkyl, alkenyl, alkynyl, aryl, cycloalkyl, $CF_3$, CN, —$OCF_3$, —$(CR^4R^5)_n$ $OR^5$, —$OR^5$, —$R^5OR^5$, —$NR^5R^6$, —$(CR^4R^5)_n NR^5R^6$, —$C(O_2)R^5$, —$C(O)R^5$, —$C(O)NR^5R^6$, —$SR^6$, —$S(O_2)R^6$, —$S(O_2)NR^5R^6$, —$N(R^5)S(O_2)R^7$, —$N(R^5)C(O)R^7$ and —$N(R^5)C(O)NR^5R^6$;

$R_3$ is selected from the group consisting of a halogen, CN, amino, alkylamino, cycloalkylamino, arylalkylamino, heteroarylamino, heteroarylalkylamino, hydroxyalkylamino, heterocycloalkylalkylamino, wherein each of said amino, alkylamino, cycloalkylamino, arylalkylamino, heteroarylamino, heteroarylalkylamino, hydroxyalkylamino, and heterocycloalkylalkylamino can be unsubstituted or optionally independently substituted with one or more moieties, which can be the same or different, each moiety being independently selected from the group consisting of halogen, alkyl, aryl, heteroaryl, cycloalkyl, heterocycloalkyl, heteroarylalkyl, heterocycloalkylalkyl, cycloalkylalkyl, $CF_3$, $OCF_3$, CN, —$OR^5$, —$NR^5R^6$, —$C(R^4R^5)_n OR^5$, —$C(O_2)R^5$, —$C(O)R^5$, —$C(O)NR^5R^6$, —$SR^6$, —$S(O_2)R^7$, —$S(O_2)NR^5R^6$, —$N(R^5)S(O_2)R^7$, —$N(R^5)C(O)R^7$ and —$N(R^5R^6)$;

$R^4$ is H, halogen, CN or alkyl;

$R^5$ is H or alkyl;

$R^6$ is selected from the group consisting of H, alkyl, aryl, arylalkyl, cycloalkyl, heterocycloalkyl, heteroaryl, and heteroarylalkyl, wherein each of said alkyl, aryl, arylalkyl, cycloalkyl, heterocycloalkyl, heteroaryl, and heteroarylalkyl can be unsubstituted or optionally substituted with one or more moieties which can be the same or different, each moiety being independently selected from the group consisting of halogen, alkyl, aryl, cycloalkyl, $CF_3$, $OCF_3$, CN, —$OR^5$, —$NR^5R^{10}$, —$N(R^5)Boc$, —$(CR^4R^5)_n OR^5$, —$C(O_2)R^5$, —$C(O)R^5$, —$C(O)NR^5R^{10}$, —$SO_3H$, —$SR^{10}$, —$S(O_2)R^7$, —$S(O_2)NR^5R^{10}$, —$N(R^5)S(O_2)R^7$, —$N(R^5)C(O)R^7$ and —$N(R^5)C(O)NR^5R^{10}$;

$R^{10}$ is selected from the group consisting of H, alkyl, aryl, arylalkyl, cycloalkyl, heterocycloalkyl, heteroaryl, and heteroarylalkyl, wherein each of said alkyl, aryl, arylalkyl, cycloalkyl, heterocycloalkyl, heteroaryl, and heteroarylalkyl can be unsubstituted or optionally substituted with one or more moieties which can be the same or different, each moiety being independently selected from the group consisting of halogen, alkyl, aryl, cycloalkyl, $CF_3$, $OCF_3$, CN, —$OR^5$, —$NR^4R^5$, —$N(R^5)Boc$, —$(CR^4R^5)_n OR^5$, —$C(O_2)R^5$, —$C(O)NR^4R^5$, —$SO_3H$, —$SR^5$, —$S(O_2)R^7$, —$S(O_2)NR^4R^5$, —$N(R^5)S(O_2)R^7$, —$N(R^5)C(O)R^7$ and —$N(R^5)C(O)NR^4R^5$; optionally (i) $R^5$ and $R^{10}$ in the moiety —$NR^5R^{10}$, or (ii) $R^5$ and $R^6$ in the moiety —$NR^5R^6$, may be joined together to form a cycloalkyl or heterocycloalkyl moiety, with each of said cycloalkyl or heterocycloalkyl moiety being unsubstituted or optionally independently being substituted with one or more $R^9$ groups;

$R^7$ is selected from the group consisting of alkyl, cycloalkyl, aryl, heterocycloalkyl, heteroaryl, arylalkyl and heteroarylalkyl, wherein each of said alkyl, cycloalkyl, aryl, heterocycloalkyl, heteroaryl, arylalkyl and heteroarylalkyl, for $R^7$ can be unsubstituted or optionally independently substituted with one or more moieties which can be the same or different, each moiety being independently selected from the group consisting of halogen, alkyl, aryl, cycloalkyl, $CF_3$, $OCF_3$, CN, —$OR^5$, —$NR^5R^{10}$, —$CH_2OR^5$, —$C(O_2)R^5$, —$C(O)NR^5R^{10}$, —$C(O)R^5$, —$SR^{10}$, —$S(O_2)R^{10}$, —$S(O_2)NR^5R^{10}$, —$N(R^5)S(O_2)R^{10}$, —$N(R^5)C(O)R^{10}$ and —$N(R^5)C(O)NR^5R^{10}$;

$R^8$ is selected from the group consisting of $R^6$, —$C(O)NR^5R^{10}$, —$CH_2OR^4$, —$C(O)OR^6$, —$C(O)R^7$ and —$S(O_2)R^7$;

$R^9$ is selected from the group consisting of halogen, —CN, —$NR^5R^6$, —$(CH_2)_n OR^4$, —$C(O_2)R^6$, —$C(O)NR^5R^6$, —$OR^6$, —$SR^6$, —$S(O_2)R^7$, —$S(O_2)NR^5R^6$, —$N(R^5)S(O_2)R^7$, —$N(R^5)C(O)R^7$ and —$N(R^5)C(O)NR^5R^6$;

m is 0 to 4; and n is 1 to 4.

The compounds of Formulas III-VII can be useful as protein kinase inhibitors and can be useful in the treatment and prevention of proliferative diseases, for example, cancer, inflammation and arthritis. They may also be useful in the treatment of neurodegenerative diseases such as Alzheimer's disease, cardiovascular diseases, viral diseases and fungal diseases.

DETAILED DESCRIPTION

In one embodiment, the present invention discloses Pyrazolo[1,5-a]pyridine compounds which are represented by structural Formula III or a pharmaceutically acceptable salt or solvate thereof, wherein the various moieties are as described above.

In another embodiment, the present invention discloses Pyrazolo[1,5-c]pyrimidine compounds which are represented by structural Formula IV or a pharmaceutically acceptable salt or solvate thereof, wherein the various moieties are as described above.

In yet another embodiment, the present invention discloses Imidazo[1,2-a]pyridine compounds which are represented by structural Formula V or a pharmaceutically acceptable salt or solvate thereof, wherein the various moieties are as described above.

In another embodiment, the present invention discloses Imidazo[1,5-a]pyrazine compounds, which are represented by structural Formula VI or a pharmaceutically acceptable salt or solvate thereof, wherein the various moieties are as described above.

In still another embodiment, the present invention discloses 2H-Indazole compounds, which are represented by structural Formula VII or a pharmaceutically acceptable salt or solvate thereof, wherein the various moieties are as described above.

An inventive group of compounds are shown in Table 1.

TABLE 1

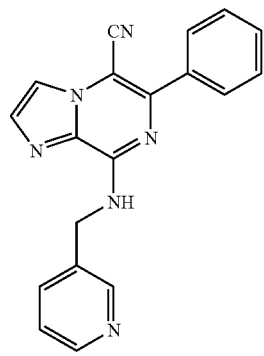

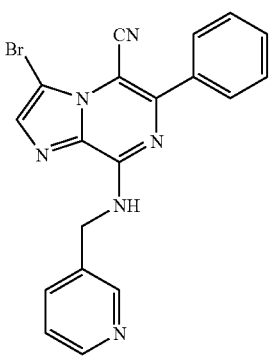

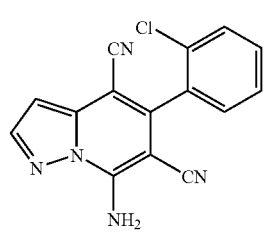

TABLE 1-continued

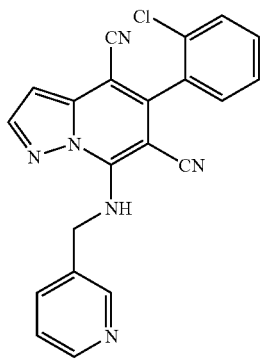

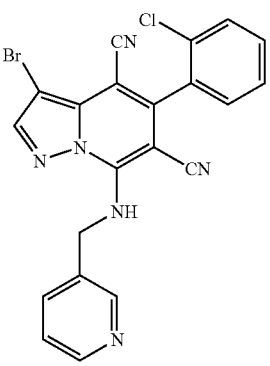

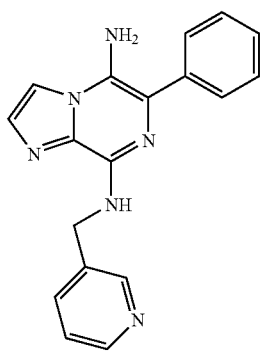

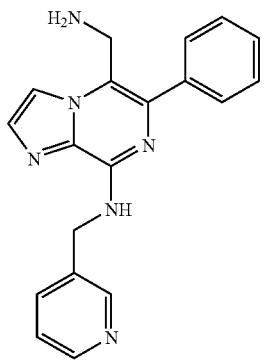

TABLE 1-continued
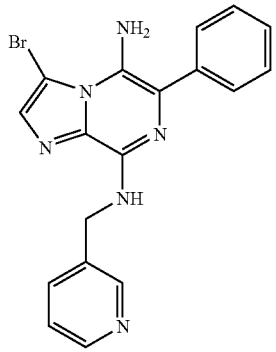
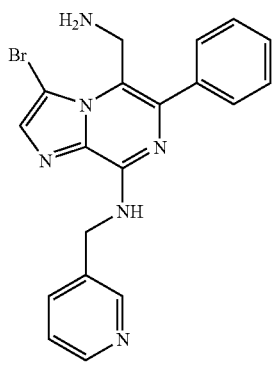
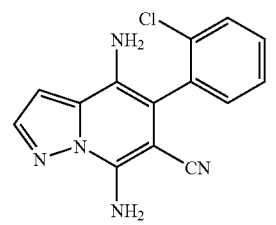
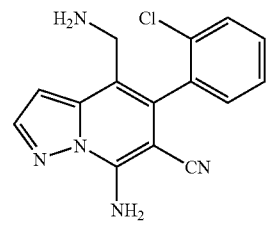
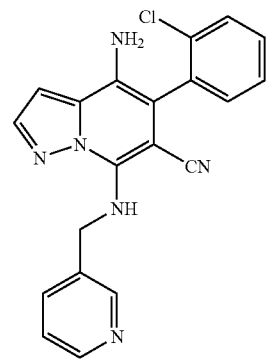
TABLE 1-continued
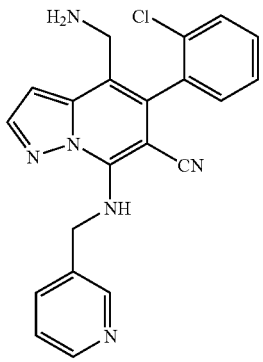
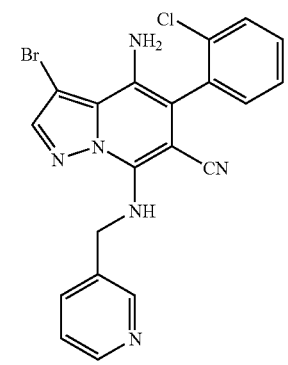
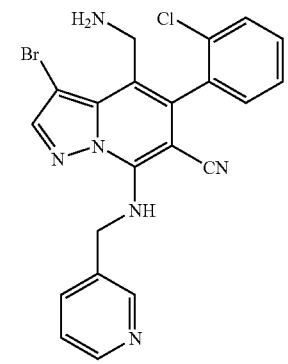
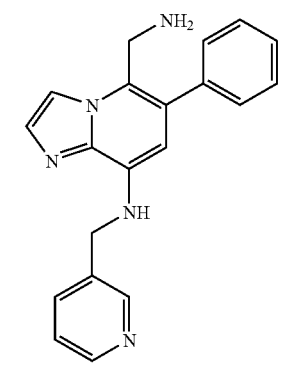

TABLE 1-continued
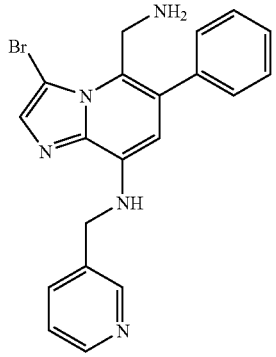
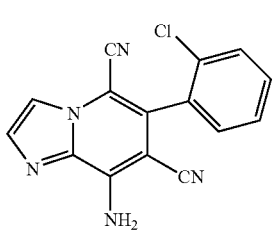
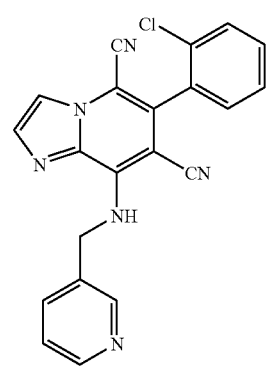
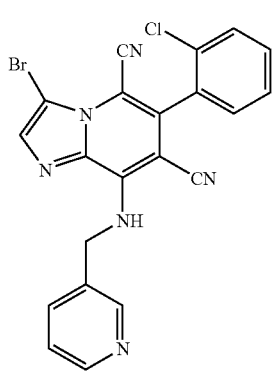
TABLE 1-continued
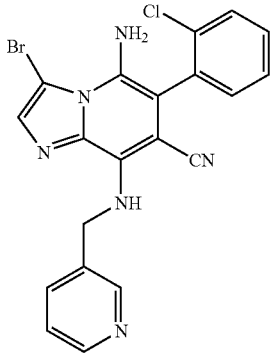
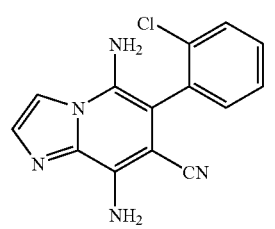
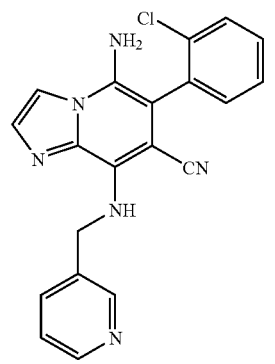
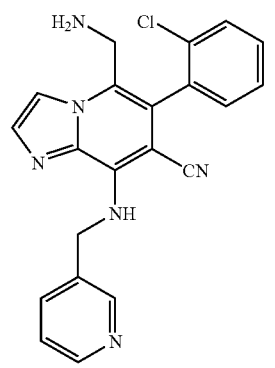

TABLE 1-continued
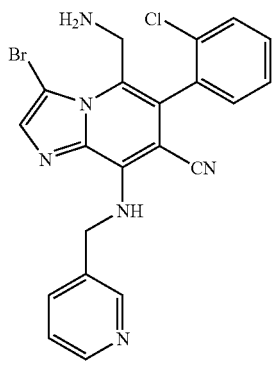
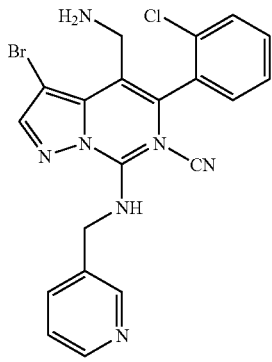
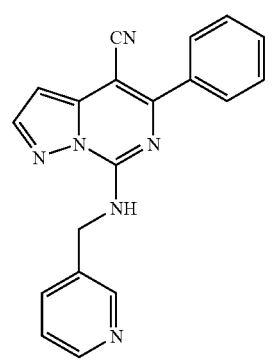
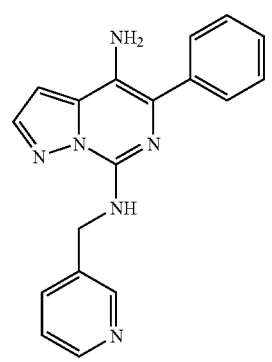
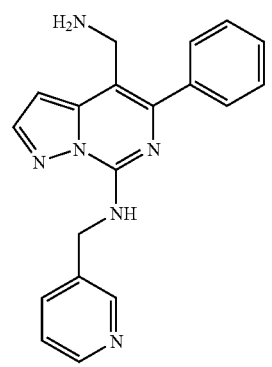

TABLE 1-continued
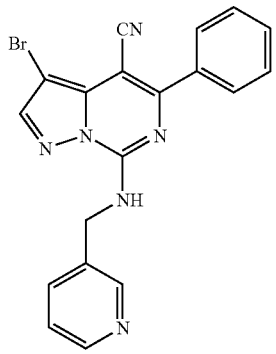
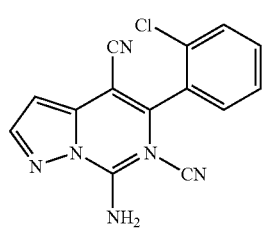
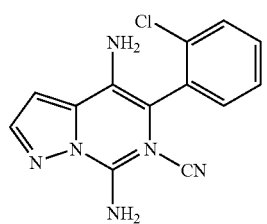
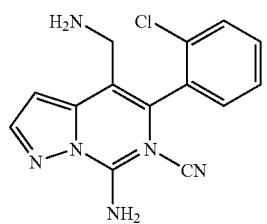
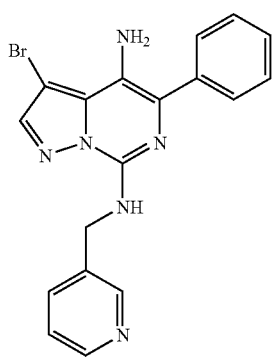
TABLE 1-continued
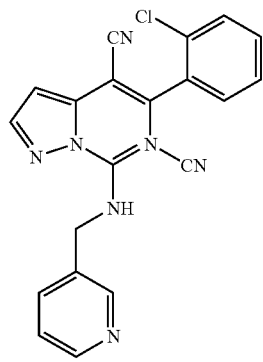
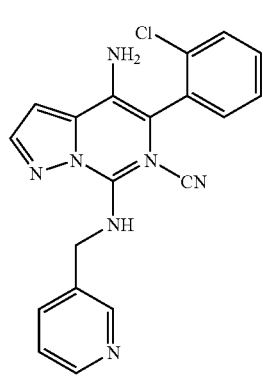
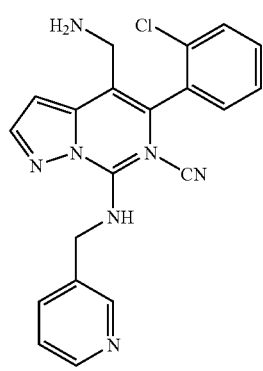
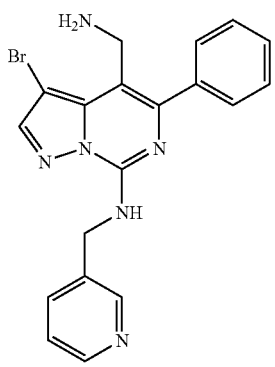

TABLE 1-continued
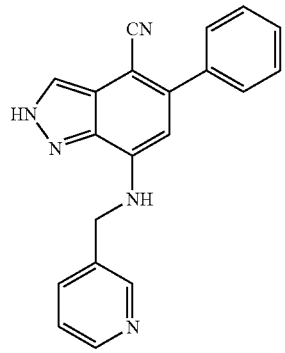
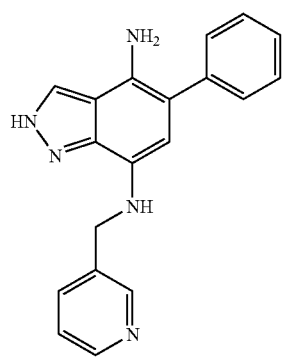
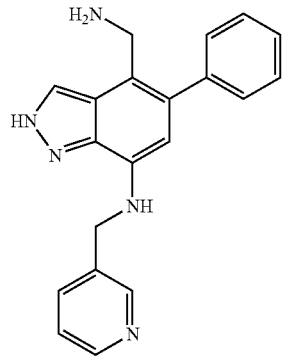
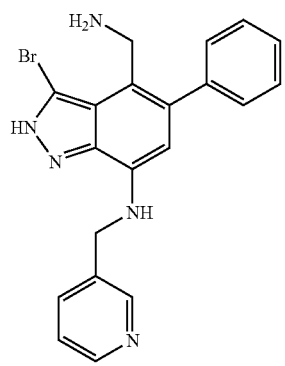
TABLE 1-continued
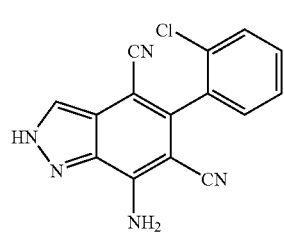
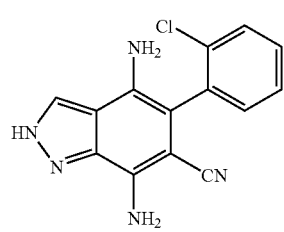
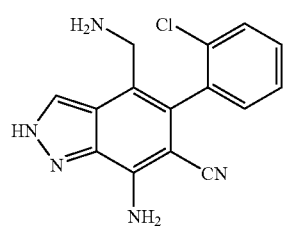
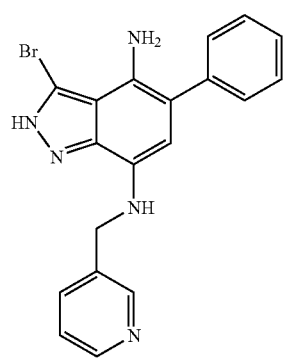
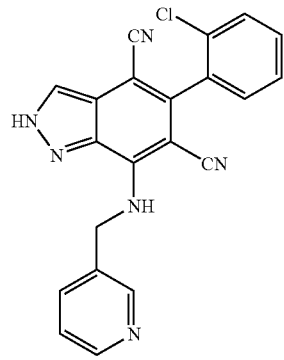

TABLE 1-continued

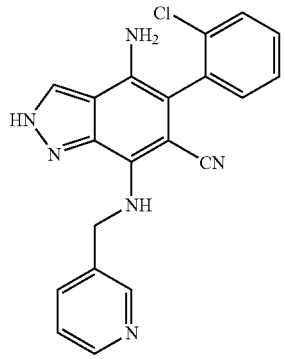

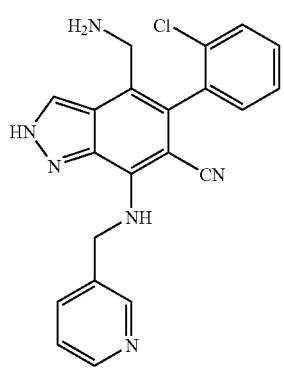

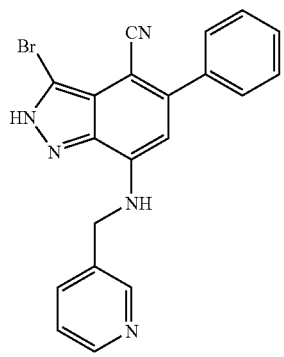

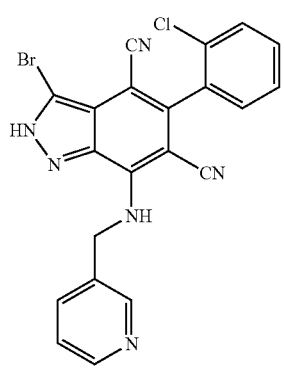

TABLE 1-continued

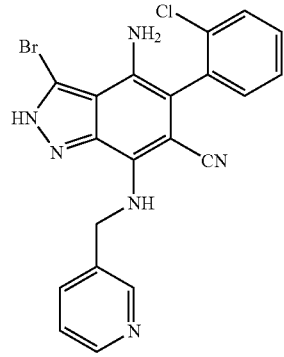

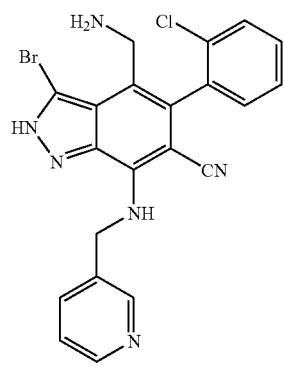

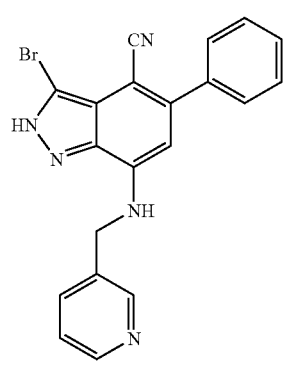

As used above, and throughout this disclosure, the following terms, unless otherwise indicated, shall be understood to have the following meanings:

"Patient" includes both human and animals.

"Mammal" means humans and other mammalian animals.

"Alkyl" means an aliphatic hydrocarbon group which may be straight or branched and comprising about 1 to about 20 carbon atoms in the chain. Preferred alkyl groups contain about 1 to about 12 carbon atoms in the chain. More preferred alkyl groups contain about 1 to about 6 carbon atoms in the chain. Branched means that one or more lower alkyl groups such as methyl, ethyl or propyl, are attached to a linear alkyl chain. "Lower alkyl" means a group having about 1 to about 6 carbon atoms in the chain which may be straight or branched. The term "substituted alkyl" means that the alkyl group may be substituted by one or more substituents which may be the same or different, each substituent being independently selected from the group consisting of halo, alkyl, aryl, cycloalkyl, cyano, hydroxy, alkoxy, alkylthio, amino, —NH (alkyl), —NH(cycloalkyl), —N(alkyl)$_2$, carboxy and —C(O)

O-alkyl. Non-limiting examples of suitable alkyl groups include methyl, ethyl, n-propyl, isopropyl and t-butyl.

"Alkenyl" means an aliphatic hydrocarbon group containing at least one carbon-carbon double bond and which may be straight or branched and comprising about 2 to about 15 carbon atoms in the chain. Preferred alkenyl groups have about 2 to about 12 carbon atoms in the chain; and more preferably about 2 to about 4 carbon atoms in the chain. Branched means that one or more lower alkyl groups such as methyl, ethyl or propyl, are attached to a linear alkenyl chain. "Lower alkenyl" means about 2 to about 6 carbon atoms in the chain which may be straight or branched. Non-limiting examples of suitable alkenyl groups include ethenyl, propenyl, 2-butenyl and 3-methylbutenyl. The term "substituted alkenyl" means that the alkenyl group may be substituted by one or more substituents which may be the same or different, each substituent being independently selected from the group consisting of alkyl, aryl and cycloalkyl.

"Alkynyl" means an aliphatic hydrocarbon group containing at least one carbon-carbon triple bond and which may be straight or branched and comprising about 2 to about 15 carbon atoms in the chain. Preferred alkynyl groups have about 2 to about 12 carbon atoms in the chain; and more preferably about 2 to about 4 carbon atoms in the chain. Branched means that one or more lower alkyl groups such as methyl, ethyl or propyl, are attached to a linear alkynyl chain. "Lower alkynyl" means about 2 to about 6 carbon atoms in the chain which may be straight or branched. Non-limiting examples of suitable alkynyl groups include ethynyl, propynyl, 2-butynyl and 3-methylbutynyl. The term "substituted alkynyl" means that the alkynyl group may be substituted by one or more substituents which may be the same or different, each substituent being independently selected from the group consisting of alkyl, aryl and cycloalkyl.

"Aryl" means an aromatic monocyclic or multicyclic ring system comprising about 6 to about 14 carbon atoms, preferably about 6 to about 10 carbon atoms. The aryl group can be optionally substituted with one or more "ring system substituents" which may be the same or different, and are as defined herein. Non-limiting examples of suitable aryl groups include phenyl and naphthyl.

"Heteroaryl" means an aromatic monocyclic or multicyclic ring system comprising about 5 to about 14 ring atoms, preferably about 5 to about 10 ring atoms, in which one or more of the ring atoms is an element other than carbon, for example nitrogen, oxygen or sulfur, alone or in combination. Preferred heteroaryls contain about 5 to about 6 ring atoms. The "heteroaryl" can be optionally substituted by one or more "ring system substituents" which may be the same or different, and are as defined herein. The prefix aza, oxa or thia before the heteroaryl root name means that at least a nitrogen, oxygen or sulfur atom respectively, is present as a ring atom. A nitrogen atom of a heteroaryl can be optionally oxidized to the corresponding N-oxide. Non-limiting examples of suitable heteroaryls include pyridyl, pyrazinyl, furanyl, thienyl, pyrimidinyl, isoxazolyl, isothiazolyl, oxazolyl, thiazolyl, pyrazolyl, furazanyl, pyrrolyl, pyrazolyl, triazolyl, 1,2,4-thiadiazolyl, pyrazinyl, pyridazinyl, quinoxalinyl, phthalazinyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl and the like.

"Aralkyl" or "arylalkyl" means an aryl-alkyl-group in which the aryl and alkyl are as previously described. Preferred aralkyls comprise a lower alkyl group. Non-limiting examples of suitable aralkyl groups include benzyl, 2-phenethyl and naphthalenylmethyl. The bond to the parent moiety is through the alkyl.

"Alkylaryl" means an alkyl-aryl-group in which the alkyl and aryl are as previously described. Preferred alkylaryls comprise a lower alkyl group. Non-limiting example of a suitable alkylaryl group is tolyl. The bond to the parent moiety is through the aryl.

"Cycloalkyl" means a non-aromatic mono- or multicyclic ring system comprising about 3 to about 10 carbon atoms, preferably about 5 to about 10 carbon atoms. Preferred cycloalkyl rings contain about 5 to about 7 ring atoms. The cycloalkyl can be optionally substituted with one or more "ring system substituents" which may be the same or different, and are as defined above. Non-limiting examples of suitable monocyclic cycloalkyls include cyclopropyl, cyclopentyl, cyclohexyl, cycloheptyl and the like. Non-limiting examples of suitable multicyclic cycloalkyls include 1-decalinyl, norbornyl, adamantyl and the like.

"Halogen" means fluorine, chlorine, bromine, or iodine. Preferred are fluorine, chlorine and bromine.

"Ring system substituent" means a substituent attached to an aromatic or non-aromatic ring system which, for example, replaces an available hydrogen on the ring system. Ring system substituents may be the same or different, each being independently selected from the group consisting of aryl, heteroaryl, aralkyl, alkylaryl, heteroaralkyl, alkylheteroaryl, hydroxy, hydroxyalkyl, alkoxy, aryloxy, aralkoxy, acyl, aroyl, halo, nitro, cyano, carboxy, alkoxycarbonyl, aryloxycarbonyl, aralkoxycarbonyl, alkylsulfonyl, arylsulfonyl, heteroarylsulfonyl, alkylthio, arylthio, heteroarylthio, aralkylthio, heteroaralkylthio, cycloalkyl, heterocyclyl, $Y_1Y_2N-$, $Y_1Y_2N$-alkyl-, $Y_1Y_2NC(O)-$ and $Y_1Y_2NSO_2-$, wherein $Y_1$ and $Y_2$ may be the same or different and are independently selected from the group consisting of hydrogen, alkyl, aryl, and aralkyl.

"Heterocyclyl" or "Heterocycloalkyl" means a non-aromatic saturated monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur, alone or in combination. There are no adjacent oxygen and/or sulfur atoms present in the ring system. Preferred heterocyclyls or heterocycloalkyls contain about 5 to about 6 ring atoms. The prefix aza, oxa or thia before the heterocyclyl or heterocycloalkyl root name means that at least a nitrogen, oxygen or sulfur atom respectively is present as a ring atom. Any —NH in a heterocyclyl ring may exist protected such as, for example, as an —N(Boc), —N(CBz), —N(Tos) group and the like; such protected moieties are also considered part of this invention. The heterocyclyl can be optionally substituted by one or more "ring system substituents" which may be the same or different, and are as defined herein. The nitrogen or sulfur atom of the heterocyclyl can be optionally oxidized to the corresponding N-oxide, S-oxide or S,S-dioxide. Non-limiting examples of suitable monocyclic heterocyclyl rings include piperidyl, pyrrolidinyl, piperazinyl, morpholinyl, thiomorpholinyl, thiazolidinyl, 1,4-dioxanyl, tetrahydrofuranyl, tetrahydrothiophenyl, and the like.

It should be noted that in hetero-atom containing ring systems of this invention, there are no hydroxyl groups on carbon atoms adjacent to a N, O or S, as well as there are no N or S groups on carbon adjacent to another heteroatom. Thus, for example, in the ring:

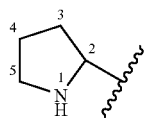

there is no —OH attached directly to carbons marked 2 and 5.

"Alkynylalkyl" means an alkynyl-alkyl-group in which the alkynyl and alkyl are as previously described. Preferred alkynylalkyls contain a lower alkynyl and a lower alkyl group. The bond to the parent moiety is through the alkyl. Non-limiting examples of suitable alkynylalkyl groups include propargylmethyl.

"Heteroaralkyl" means a heteroaryl-alkyl-group in which the heteroaryl and alkyl are as previously described. Preferred heteroaralkyls contain a lower alkyl group. Non-limiting examples of suitable aralkyl groups include pyridylmethyl, and quinolin-3-ylmethyl. The bond to the parent moiety is through the alkyl.

"Hydroxyalkyl" means a HO-alkyl-group in which alkyl is as previously defined. Preferred hydroxyalkyls contain lower alkyl. Non-limiting examples of suitable hydroxyalkyl groups include hydroxymethyl and 2-hydroxyethyl.

"Acyl" means an H—C(O)—, alkyl-C(O)— or cycloalkyl-C(O)—, group in which the various groups are as previously described. The bond to the parent moiety is through the carbonyl. Preferred acyls contain a lower alkyl. Non-limiting examples of suitable acyl groups include formyl, acetyl and propanoyl.

"Aroyl" means an aryl-C(O)— group in which the aryl group is as previously described. The bond to the parent moiety is through the carbonyl. Non-limiting examples of suitable groups include benzoyl and 1-naphthoyl.

"Alkoxy" means an alkyl-O— group in which the alkyl group is as previously described. Non-limiting examples of suitable alkoxy groups include methoxy, ethoxy, n-propoxy, isopropoxy and n-butoxy. The bond to the parent moiety is through the ether oxygen.

"Aryloxy" means an aryl-O— group in which the aryl group is as previously described. Non-limiting examples of suitable aryloxy groups include phenoxy and naphthoxy. The bond to the parent moiety is through the ether oxygen.

"Aralkyloxy" means an aralkyl-O— group in which the aralkyl group is as previously described. Non-limiting examples of suitable aralkyloxy groups include benzyloxy and 1- or 2-naphthalenemethoxy. The bond to the parent moiety is through the ether oxygen.

"Alkylthio" means an alkyl-S— group in which the alkyl group is as previously described. Non-limiting examples of suitable alkylthio groups include methylthio and ethylthio. The bond to the parent moiety is through the sulfur.

"Arylthio" means an aryl-S— group in which the aryl group is as previously described. Non-limiting examples of suitable arylthio groups include phenylthio and naphthylthio. The bond to the parent moiety is through the sulfur.

"Aralkylthio" means an aralkyl-S— group in which the aralkyl group is as previously described. Non-limiting example of a suitable aralkylthio group is benzylthio. The bond to the parent moiety is through the sulfur.

"Alkoxycarbonyl" means an alkyl-O—CO— group. Non-limiting examples of suitable alkoxycarbonyl groups include methoxycarbonyl and ethoxycarbonyl. The bond to the parent moiety is through the carbonyl.

"Aryloxycarbonyl" means an aryl-O—C(O)— group. Non-limiting examples of suitable aryloxycarbonyl groups include phenoxycarbonyl and naphthoxycarbonyl. The bond to the parent moiety is through the carbonyl.

"Aralkoxycarbonyl" means an aralkyl-O—C(O)— group. Non-limiting example of a suitable aralkoxycarbonyl group is benzyloxycarbonyl. The bond to the parent moiety is through the carbonyl.

"Alkylsulfonyl" means an alkyl-$S(O_2)$— group. Preferred groups are those in which the alkyl group is lower alkyl. The bond to the parent moiety is through the sulfonyl.

"Arylsulfonyl" means an aryl-$S(O_2)$— group. The bond to the parent moiety is through the sulfonyl.

The term "substituted" means that one or more hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds. By "stable compound" or "stable structure" is meant a compound that is sufficiently robust to survive isolation to a useful degree of purity from a reaction mixture, and formulation into an efficacious therapeutic agent.

The term "optionally substituted" means optional substitution with the specified groups, radicals or moieties.

It should also be noted that any heteroatom with unsatisfied valences in the text, schemes, examples and Tables herein is assumed to have the hydrogen atom to satisfy the valences.

When a functional group in a compound is termed "protected", this means that the group is in modified form to preclude undesired side reactions at the protected site when the compound is subjected to a reaction. Suitable protecting groups will be recognized by those with ordinary skill in the art as well as by reference to standard textbooks such as, for example, T. W. Greene et al, *Protective Groups in organic Synthesis* (1991), Wiley, N.Y.

When any variable (e.g., aryl, heterocycle, $R^2$, etc.) occurs more than one time in any constituent or Formula of this invention, its definition on each occurrence is independent of its definition at every other occurrence.

As used herein, the term "composition" is intended to encompass a product comprising the specified ingredients in the specified amounts, as well as any product which results, directly or indirectly, from combination of the specified ingredients in the specified amounts.

Prodrugs and solvates of the compounds of the invention are also contemplated herein. The term "prodrug", as employed herein, denotes a compound that is a drug precursor, which, upon administration to a subject, undergoes chemical conversion by metabolic or chemical processes to yield a compound of this invention or a salt and/or solvate thereof. A discussion of prodrugs is provided in T. Higuchi and V. Stella, *Pro-drugs as Novel Delivery Systems* (1987) 14 of the A.C.S. Symposium Series, and in *Bioreversible Carriers in Drug Design*, (1987) Edward B. Roche, ed., American Pharmaceutical Association and Pergamon Press, both of which are incorporated herein by reference thereto.

"Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. "Hydrate" is a solvate wherein the solvent molecule is H₂O.

"Effective amount" or "therapeutically effective amount" is meant to describe an amount of compound or a composition of the present invention effective in inhibiting the CDK(s) and thus producing the desired therapeutic, ameliorative, inhibitory or preventative effect.

The compounds of this invention can form salts, which are also within the scope of this invention. Reference to a compound of this invention herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a compound of this invention contains both a basic moiety, such as, but not limited to a pyridine or imidazole, and an acidic moiety, such as, but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also useful. Salts of the compounds of this invention may be formed, for example, by reacting a compound of this invention with an amount of acid or base, such as an equivalent amount, in a medium such as one in which the salt precipitates or in an aqueous medium followed by lyophilization. Acids (and bases) which are generally considered suitable for the formation of pharmaceutically useful salts from basic (or acidic) pharmaceutical compounds are discussed, for example, by S. Berge et al, *Journal of Pharmaceutical Sciences* (1977) 66(1)1-19; P. Gould, *Intentional J. of Pharmaceutics* (1986) 33 201-217; Anderson et al, *The Practice of Medicinal Chemistry* (1996), Academic Press, New York; in *The Orange Book* (Food & Drug Administration, Washington, D.C. on their website); and P. Heinrich Stahl, Camille G. Wermuth (Eds.), *Handbook of Pharmaceutical Salts: Properties, Selection, and Use*, (2002) Int'l. Union of Pure and Applied Chemistry, pp. 330-331. These disclosures are incorporated herein by reference thereto.

Exemplary acid addition salts include acetates, adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides, hydrobromides, hydroiodides, 2-hydroxyethanesulfonates, lactates, maleates, methanesulfonates, methyl sulfates, 2-naphthalenesulfonates, nicotinates, nitrates, oxalates, pamoates, pectinates, persulfates, 3-phenylpropionates, phosphates, picrates, pivalates, propionates, salicylates, succinates, sulfates, sulfonates (such as those mentioned herein), tartarates, thiocyanates, toluenesulfonates (also known as tosylates), undecanoates, and the like.

Exemplary basic salts include ammonium salts, alkali metal salts such as sodium, lithium, and potassium salts, alkaline earth metal salts such as calcium and magnesium salts, aluminum salts, zinc salts, salts with organic bases (for example, organic amines) such as benzathines, diethylamine, dicyclohexylamines, hydrabamines (formed with N,N-bis (dehydroabietyl)ethylenediamine), N-methyl-D-glucamines, N-methyl-D-glucamides, t-butyl amines, piperazine, phenylcyclohexylamine, choline, tromethamine, and salts with amino acids such as arginine, lysine and the like. Basic nitrogen-containing groups may be quaternized with agents such as lower alkyl halides (e.g. methyl, ethyl, propyl, and butyl chlorides, bromides and iodides), dialkyl sulfates (e.g. dimethyl, diethyl, dibutyl, and diamyl sulfates), long chain halides (e.g. decyl, lauryl, myristyl and stearyl chlorides, bromides and iodides), aralkyl halides (e.g. benzyl and phenethyl bromides), and others.

All such acid salts and base salts are intended to be pharmaceutically acceptable salts within the scope of the invention and all acid and base salts are considered equivalent to the free forms of the corresponding compounds for purposes of the invention.

Compounds of this invention, and salts, solvates and prodrugs thereof, may exist in their tautomeric form (for example, as an amide or imino ether). All such tautomeric forms are contemplated herein as part of the present invention.

All stereoisomers (for example, geometric isomers, optical isomers and the like) of the present compounds (including those of the salts, solvates and prodrugs of the compounds as well as the salts and solvates of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention. Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the IUPAC 1974 Recommendations. The use of the terms "salt", "solvate" "prodrug" and the like, is intended to equally apply to the salt, solvate and prodrug of enantiomers, stereoisomers, rotamers, tautomers, racemates or prodrugs of the inventive compounds.

The compounds according to the invention have pharmacological properties; in particular, the compounds of this invention can be inhibitors of protein kinases such as the cyclin dependent kinases (CDKs), for example, CDC2 (CDK1), CDK2, CDK4, CDK5, CDK6, CDK7 and CDK8. The novel compounds of this invention are expected to be useful in the therapy of proliferative diseases such as cancer, autoimmune diseases, viral diseases, fungal diseases, neurological/neurodegenerative disorders, arthritis, inflammation, anti-proliferative (e.g., ocular retinopathy), neuronal, alopecia and cardiovascular disease. Many of these diseases and disorders are listed in U.S. Pat. No. 6,413,974 cited earlier, the disclosure of which is incorporated herein.

More specifically, the compounds of this invention can be useful in the treatment of a variety of cancers, including (but not limited to) the following: carcinoma, including that of the bladder, breast, colon, kidney, liver, lung, including small cell lung cancer, esophagus, gall bladder, ovary, pancreas, stomach, cervix, thyroid, prostate, and skin, including squamous cell carcinoma;

hematopoietic tumors of lymphoid lineage, including leukemia, acute lymphocytic leukemia, acute lymphoblastic leukemia, B-cell lymphoma, T-cell lymphoma, Hodgkins lymphoma, non-Hodgkins lymphoma, hairy cell lymphoma and Burkett's lymphoma;

hematopoietic tumors of myeloid lineage, including acute and chronic myelogenous leukemias, myelodysplastic syndrome and promyelocytic leukemia;

tumors of mesenchymal origin, including fibrosarcoma and rhabdomyosarcoma;

tumors of the central and peripheral nervous system, including astrocytoma, neuroblastoma, glioma and schwannomas; and other tumors, including melanoma, seminoma, teratocarcinoma, osteosarcoma, xenoderoma pigmentosum, keratocanthoma, thyroid follicular cancer and Kaposi's sarcoma.

Due to the key role of CDKs in the regulation of cellular proliferation in general, inhibitors could act as reversible cytostatic agents which may be useful in the treatment of any disease process which features abnormal cellular proliferation, e.g., benign prostate hyperplasia, familial adenomatosis polyposis, neuro-fibromatosis, atherosclerosis, pulmonary fibrosis, arthritis, psoriasis, glomerulonephritis, restenosis following angioplasty or vascular surgery, hypertrophic scar formation, inflammatory bowel disease, transplantation rejection, endotoxic shock, and fungal infections.

Compounds of this invention may also be useful in the treatment of Alzheimer's disease, as suggested by the recent finding that CDK5 is involved in the phosphorylation of tau protein (J. Biochem, (1995) 117, 741-749).

Compounds of this invention may induce or inhibit apoptosis. The apoptotic response is aberrant in a variety of human diseases. Compounds of this invention, as modulators of apoptosis, will be useful in the treatment of cancer (including but not limited to those types mentioned hereinabove), viral infections (including but not limited to herpesvirus, poxvirus, Epstein-Barr virus, Sindbis virus and adenovirus), prevention of AIDS development in HIV-infected individuals, autoimmune diseases (including but not limited to systemic lupus, erythematosus, autoimmune mediated glomerulonephritis, rheumatoid arthritis, psoriasis, inflammatory bowel disease, and autoimmune diabetes mellitus), neurodegenerative disorders (including but not limited to Alzheimer's disease, AIDS-related dementia, Parkinson's disease, amyotrophic lateral sclerosis, retinitis pigmentosa, spinal muscular atrophy and cerebellar degeneration), myelodysplastic syndromes, aplastic anemia, ischemic injury associated with myocardial infarctions, stroke and reperfusion injury, arrhythmia, atherosclerosis, toxin-induced or alcohol related liver diseases, hematological diseases (including but not limited to chronic anemia and aplastic anemia), degenerative diseases of the musculoskeletal system (including but not limited to osteoporosis and arthritis) aspirin-sensitive rhinosinusitis, cystic fibrosis, multiple sclerosis, kidney diseases and cancer pain.

Compounds of this invention, as inhibitors of the CDKs, can modulate the level of cellular RNA and DNA synthesis. These agents would therefore be useful in the treatment of viral infections (including but not limited to HIV, human papilloma virus, herpesvirus, poxvirus, Epstein-Barr virus, Sindbis virus and adenovirus).

Compounds of this invention may also be useful in the chemoprevention of cancer. Chemoprevention is defined as inhibiting the development of invasive cancer by either blocking the initiating mutagenic event or by blocking the progression of pre-malignant cells that have already suffered an insult or inhibiting tumor relapse.

Compounds of this invention may also be useful in inhibiting tumor angiogenesis and metastasis.

Compounds of this invention may also act as inhibitors of other protein kinases, e.g., protein kinase C, her2, raf 1, MEK1, MAP kinase, EGF receptor, PDGF receptor, IGF receptor, PI3 kinase, wee1 kinase, Src, Abl and thus be effective in the treatment of diseases associated with other protein kinases.

Another aspect of this invention is a method of treating a mammal (e.g., human) having a disease or condition associated with the CDKs by administering a therapeutically effective amount of at least one compound of this invention, or a pharmaceutically acceptable salt or solvate of said compound to the mammal.

A preferred dosage is about 0.001 to 500 mg/kg of body weight/day of the compound of this invention. An especially preferred dosage is about 0.01 to 25 mg/kg of body weight/day of a compound of this invention, or a pharmaceutically acceptable salt or solvate of said compound.

The compounds of this invention may also be useful in combination (administered together or sequentially) with one or more of anti-cancer treatments such as radiation therapy, and/or one or more anti-cancer agents selected from the group consisting of cytostatic agents, cytotoxic agents (such as for example, but not limited to, DNA interactive agents (such as cisplatin or doxorubicin)); taxanes (e.g. taxotere, taxol); topoisomerase II inhibitors (such as etoposide); topoisomerase I inhibitors (such as irinotecan (or CPT-11), camptostar, or topotecan); tubulin interacting agents (such as paclitaxel, docetaxel or the epothilones); hormonal agents (such as tamoxifen); thymidilate synthase inhibitors (such as 5-fluorouracil); anti-metabolites (such as methotrexate); alkylating agents (such as temozolomide (TEMODAR™ from Schering-Plough Corporation, Kenilworth, N.J.), cyclophosphamide); Farnesyl protein transferase inhibitors (such as, SARASAR™ (4-[2-[4-[(11R)-3,10-dibromo-8-chloro-6,11-dihydro-5H-benzo[5,6]cyclohepta[1,2-b]pyridin-11-yl-]-1-piperidinyl]-2-oxoethyl]-1-piperidinecarboxamide, or SCH 66336 from Schering-Plough Corporation, Kenilworth, N.J.), tipifarnib (Zarnestra® or R115777 from Janssen Pharmaceuticals), L778, 123 (a farnesyl protein transferase inhibitor from Merck & Company, Whitehouse Station, N.J.), BMS 214662 (a farnesyl protein transferase inhibitor from Bristol-Myers Squibb Pharmaceuticals, Princeton, N.J.); signal transduction inhibitors (such as, Iressa (from Astra Zeneca Pharmaceuticals, England), Tarceva (EGFR kinase inhibitors), antibodies to EGFR (e.g., C225), GLEEVEC™ (C-abl kinase inhibitor from Novartis Pharmaceuticals, East Hanover, N.J.); interferons such as, for example, intron (from Schering-Plough Corporation), Peg-Intron (from Schering-Plough Corporation); hormonal therapy combinations; aromatase combinations; ara-C, adriamycin, cytoxan, and gemcitabine.

Other anti-cancer (also known as anti-neoplastic) agents include but are not limited to Uracil mustard, Chlormethine, Ifosfamide, Melphalan, Chlorambucil, Pipobroman, Triethylenemelamine, Triethylenethiophosphoramine, Busulfan, Carmustine, Lomustine, Streptozocin, Dacarbazine, Floxuridine, Cytarabine, 6-Mercaptopurine, 6-Thioguanine, Fludarabine phosphate, oxaliplatin, leucovirin, oxaliplatin (ELOXATIN™ from Sanofi-Synthelabo Pharmaeuticals, France), Pentostatine, Vinblastine, Vincristine, Vindesine, Bleomycin, Dactinomycin, Daunorubicin, Doxorubicin, Epirubicin, Idarubicin, Mithramycin, Deoxycoformycin, Mitomycin-C, L-Asparaginase, Teniposide 17□-Ethinylestradiol, Diethylstilbestrol, Testosterone, Prednisone, Fluoxymesterone, Dromostanolone propionate, Testolactone, Megestrolacetate, Methylprednisolone, Methyltestosterone, Prednisolone, Triamcinolone, Chlorotrianisene, Hydroxyprogesterone, Aminoglutethimide, Estramustine, Medroxyprogesteroneacetate, Leuprolide, Flutamide, Toremifene, goserelin, Cisplatin, Carboplatin, Hydroxyurea, Amsacrine, Procarbazine, Mitotane, Mitoxantrone, Levamisole, Navelbene, Anastrozole, Letrazole, Capecitabine, Reloxafine, Droloxafine, or Hexamethylmelamine.

If formulated as a fixed dose, such combination products employ the compounds of this invention within the dosage range described herein and the other pharmaceutically active agent or treatment within its dosage range. For example, the CDC2 inhibitor olomucine has been found to act synergistically with known cytotoxic agents in inducing apoptosis (*J. Cell Sci.*, (1995) 108, 2897. Compounds of this invention may also be administered sequentially with known anticancer or cytotoxic agents when a combination formulation is inappropriate. The invention is not limited in the sequence of administration; compounds of this invention may be administered either prior to or after administration of the known anticancer or cytotoxic agent. For example, the cytotoxic activity of the cyclin-dependent kinase inhibitor flavopiridol is affected by the sequence of administration with anticancer agents. *Cancer Research*, (1997) 57, 3375. Such techniques are within the skills of persons skilled in the art as well as attending physicians.

Accordingly, in an aspect, this invention includes combinations comprising an amount of at least one compound of this invention, or a pharmaceutically acceptable salt or solvate thereof, and an amount of one or more anti-cancer treatments and anti-cancer agents listed above wherein the amounts of the compounds/treatments result in desired therapeutic effect.

The pharmacological properties of the compounds of this invention may be confirmed by a number of pharmacological assays. The exemplified pharmacological assays, which are described later have been carried out with the compounds according to the invention and their salts.

This invention is also directed to pharmaceutical compositions, which comprise at least one of the compounds of this invention, or a pharmaceutically acceptable salt or solvate of said compound and at least one pharmaceutically acceptable carrier.

For preparing pharmaceutical compositions from the compounds described by this invention, inert, pharmaceutically acceptable carriers can be either solid or liquid. Solid form preparations include powders, tablets, dispersible granules, capsules, cachets and suppositories. The powders and tablets may be comprised of from about 5 to about 95 percent active ingredient. Suitable solid carriers are known in the art, e.g., magnesium carbonate, magnesium stearate, talc, sugar or lactose. Tablets, powders, cachets and capsules can be used as solid dosage forms suitable for oral administration. Examples of pharmaceutically acceptable carriers and methods of manufacture for various compositions may be found in A. Gennaro (ed.), *Remington's Pharmaceutical Sciences*, 18$^{th}$ Edition, (1990), Mack Publishing Co., Easton, Pa.

Liquid form preparations include solutions, suspensions and emulsions. As an example may be mentioned water or water-propylene glycol solutions for parenteral injection or addition of sweeteners and opacifiers for oral solutions, suspensions and emulsions. Liquid form preparations may also include solutions for intranasal administration.

Aerosol preparations suitable for inhalation may include solutions and solids in powder form, which may be in combination with a pharmaceutically acceptable carrier, such as an inert compressed gas, e.g. nitrogen.

Also included are solid form preparations that are intended to be converted, shortly before use, to liquid form preparations for either oral or parenteral administration. Such liquid forms include solutions, suspensions and emulsions.

The compounds of the invention may also be deliverable transdermally. The transdermal compositions can take the form of creams, lotions, aerosols and/or emulsions and can be included in a transdermal patch of the matrix or reservoir type as are conventional in the art for this purpose.

The compounds of this invention may also be delivered subcutaneously.

Preferably the compound is administered orally.

Preferably, the pharmaceutical preparation is in a unit dosage form. In such form, the preparation is subdivided into suitably sized unit doses containing appropriate quantities of the active component, e.g., an effective amount to achieve the desired purpose.

The quantity of active compound in a unit dose of preparation may be varied or adjusted from about 1 mg to about 100 mg, preferably from about 1 mg to about 50 mg, more preferably from about 1 mg to about 25 mg, according to the particular application.

The actual dosage employed may be varied depending upon the requirements of the patient and the severity of the condition being treated. Determination of the proper dosage regimen for a particular situation is within the skill of the art. For convenience, the total daily dosage may be divided and administered in portions during the day as required.

The amount and frequency of administration of the compounds of the invention and/or the pharmaceutically acceptable salts thereof will be regulated according to the judgment of the attending clinician considering such factors as age, condition and size of the patient as well as severity of the symptoms being treated. A typical recommended daily dosage regimen for oral administration can range from about 1 mg/day to about 500 mg/day, preferably 1 mg/day to 200 mg/day, in two to four divided doses.

Another aspect of this invention is a kit comprising a therapeutically effective amount of at least one compound of this invention, or a pharmaceutically acceptable salt or solvate of said compound and a pharmaceutically acceptable carrier, vehicle or diluent.

Yet another aspect of this invention is a kit comprising an amount of at least one compound of this invention, or a pharmaceutically acceptable salt or solvate of said compound and an amount of at least one anticancer therapy and/or anticancer agent listed above, wherein the amounts of the two or more ingredients result in desired therapeutic effect.

The invention disclosed herein is exemplified by the following preparations and examples, which should not be construed to limit the scope of the disclosure. Alternative mechanistic pathways and analogous structures will be apparent to those skilled in the art.

Where NMR data are presented, $^1$H spectra were obtained on either a Varian VXR-200 (200 MHz, $^1$H), Varian Gemini-300 (300 MHz) or XL-400 (400 MHz) and are reported as ppm down field from Me$_4$Si with number of protons, multiplicities, and coupling constants in Hertz indicated parenthetically. Where LC/MS data are presented, analyses was performed using an Applied Biosystems API-100 mass spectrometer and Shimadzu SCL-10A LC column: Altech platinum C18, 3 micron, 33 mm×7 mm ID; gradient flow: 0 min—10% CH$_3$CN, 5 min—95% CH$_3$CN, 7 min—95% CH$_3$CN, 7.5 min—10% CH$_3$CN, 9 min—stop. The retention time and observed parent ion are given.

The following solvents, reagents, conditions, and techniques may be referred to by their abbreviations:

Thin layer chromatography: TLC dichloromethane: CH$_2$Cl$_2$ ethyl acetate: AcOEt or EtOAc methanol: MeOH trifluoroacetate: TFA triethylamine: Et$_3$N or TEA butoxycarbonyl: n-Boc or Boc nuclear magnetic resonance spectroscopy: NMR liquid chromatography mass spectrometry: LCMS high resolution mass spectrometry: HRMS milliliters: mL millimoles: mmol microliters: μl grams: g milligrams: mg room temperature or rt (ambient): about 25° C.

Compounds of this invention can be prepared by known methods from starting materials either known in the art or prepared by methods known in the art.

Compounds of the present invention can be prepared by several methods. Non-limiting examples of suitable methods are illustrated in the schemes below.

EXAMPLES

The compounds of the present invention can be prepared through the general routes described below.

Synthesis of pyrazolo[1,5-a]pyridines (Formula III) is described below in Scheme 1.

R is defined above.

Alternative synthesis of intermediate 2 is illustrated in Scheme 1a:

-continued

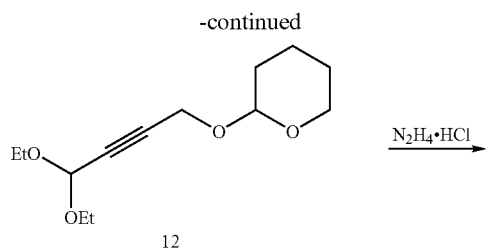
12

N₂H₄·HCl →

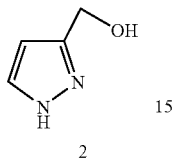
2

Generally, one method of preparing a pyrazolo[1,5-a]pyridine involves combining (1H-Pyrazol-3-yl)-acetonitrile with 2-Benzylidene-malononitrile to form a 7-amino substituted pyrazolo[1,5-a]pyridine that is further reacted with the appropriate aldehyde to achieve the target pyrazolo[1,5-a]pyridine as shown in Schemes 1 and 1a.

Another method to synthesize a pyrazolo[1,5-a]pyridine is illustrated in Scheme 1b.

Scheme 1b

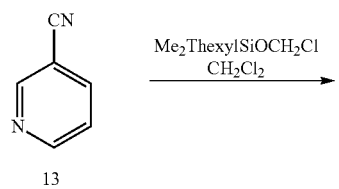
13

Me₂ThexylSiOCH₂Cl
CH₂Cl₂ →

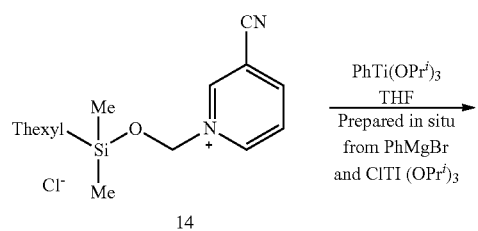
14

PhTi(OPrⁱ)₃
THF
Prepared in situ
from PhMgBr
and ClTi(OPrⁱ)₃ →

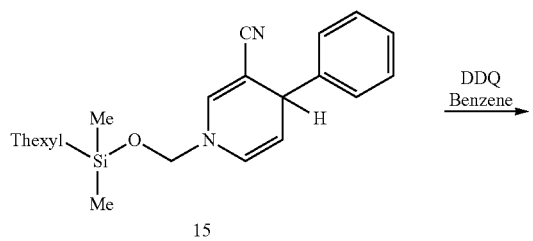
15

DDQ
Benzene →

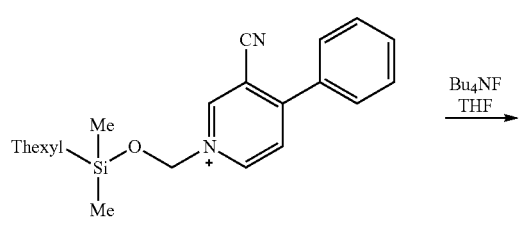
16

Bu₄NF
THF →

-continued

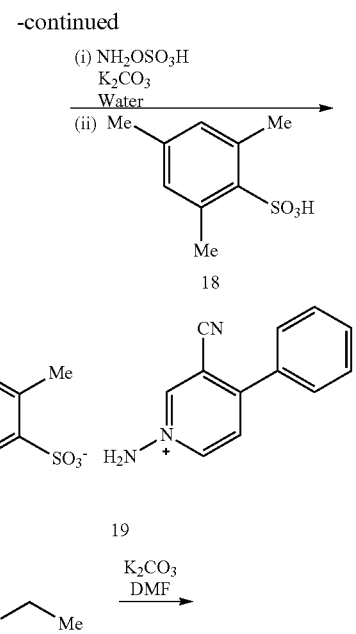
17

(i) NH₂OSO₃H
K₂CO₃
Water
(ii) 
18 →

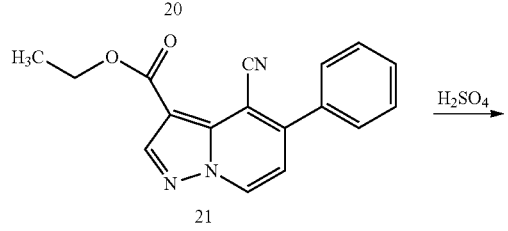
19

+

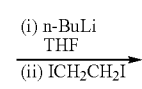
20

K₂CO₃
DMF →

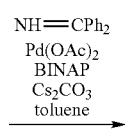
21

H₂SO₄ →

22

(i) n-BuLi
THF
(ii) ICH₂CH₂I →

23

NH=CPh₂
Pd(OAc)₂
BINAP
Cs₂CO₃
toluene →

24

NBS
CH₃CN →

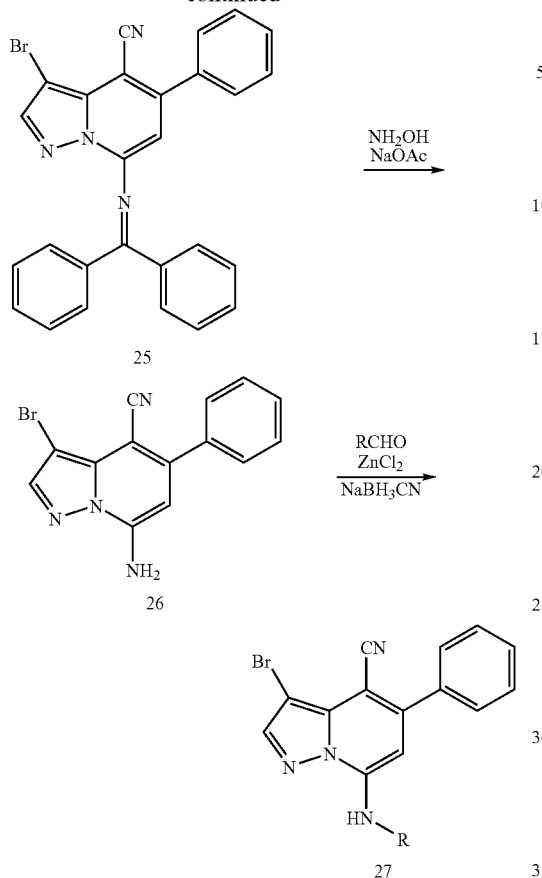
Scheme 1c illustrates an alternative route to intermediate 17, 3-cyano-4-phenyl pyridine.
Scheme 1d illustrates a chlorinated form of intermediate 17, 3-cyano-4-phenyl pyridine.
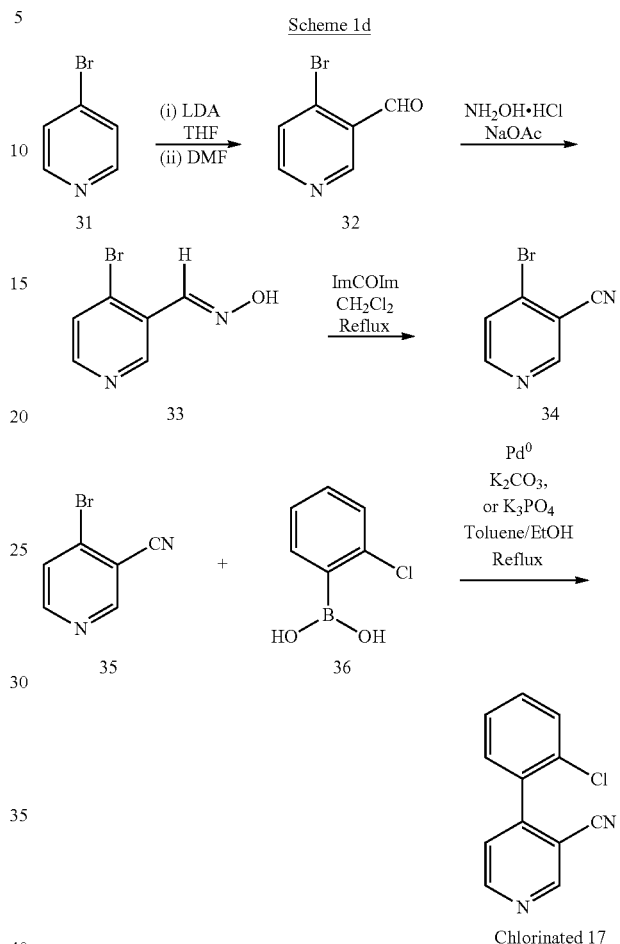
An alternative route to target pyrazolo[1,5-a]pyridine is illustrated in Scheme 1e.
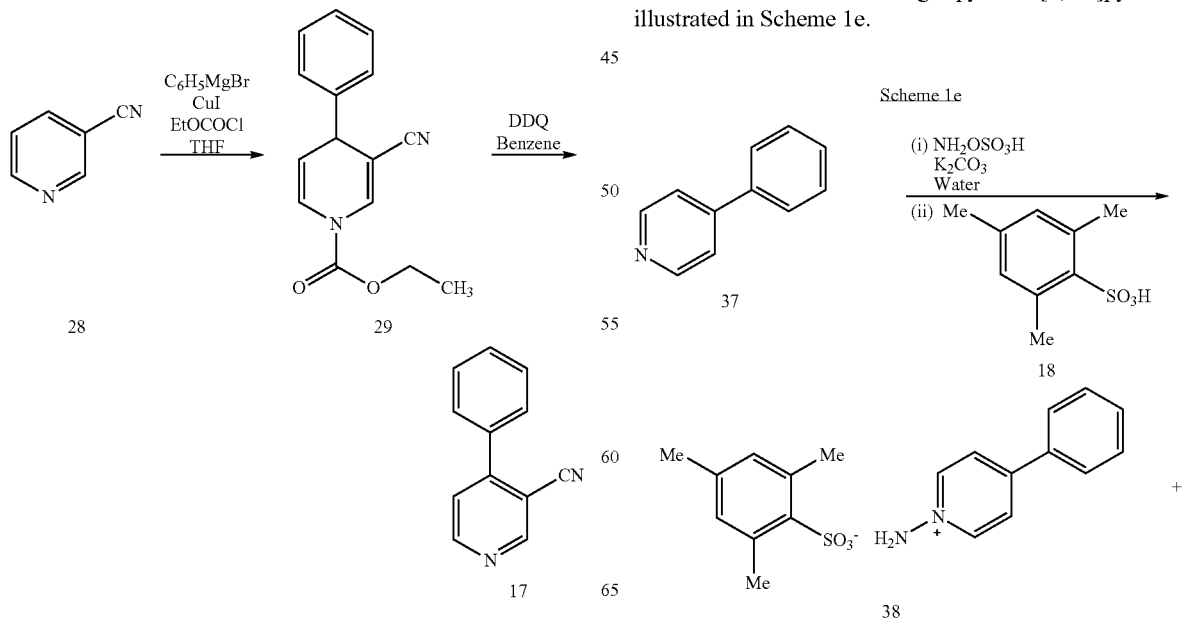

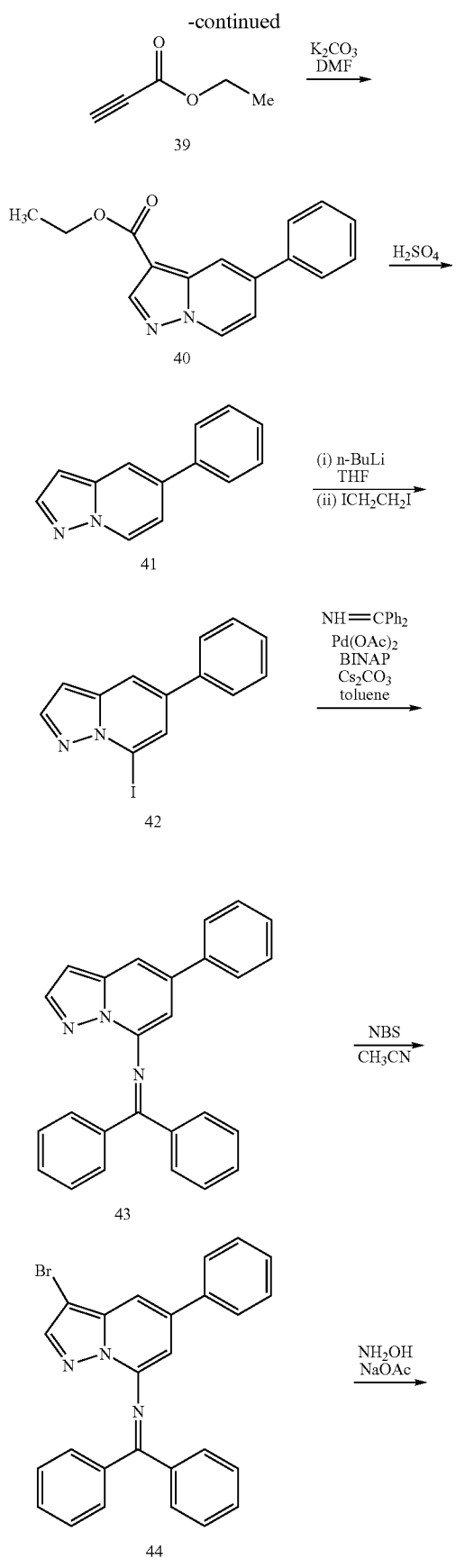
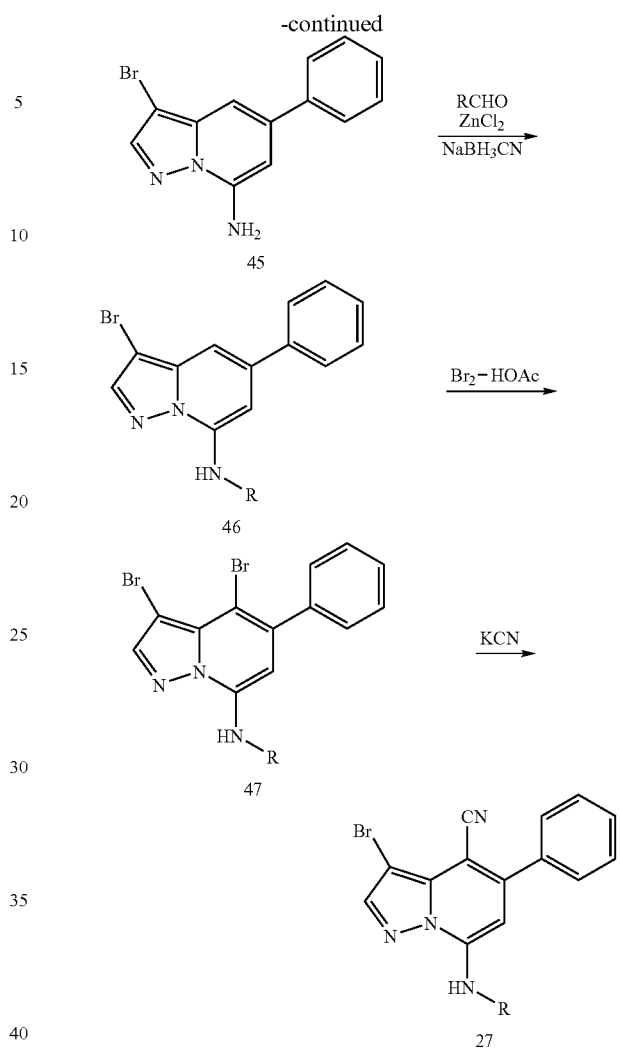

An unsubstituted phenyl pyridine instead of the 3-cyano-4-phenyl pyridine as shown in Schemes 1b-d can be used in the synthesis of the carbonitrile substituted target pyrazolo [1,5-a]pyridine. In which case, the cyano group is added during the last steps of the synthesis by brominating the 4 position then substituting the bromine with a carbonitrile group as shown in Scheme 1e.

A 4-methylamino pyrazolo [1,5-a]pyridine derivative is formed by reducing the 4-cyano group using lithium aluminum hydride as shown in scheme 1f.

Scheme 1f

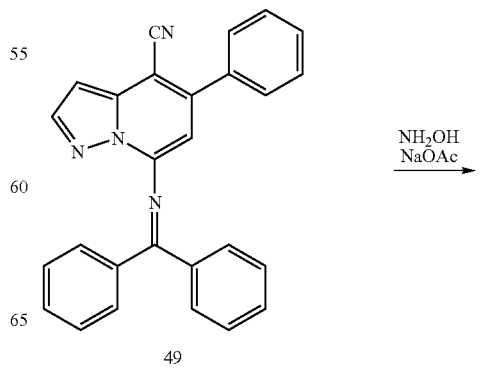

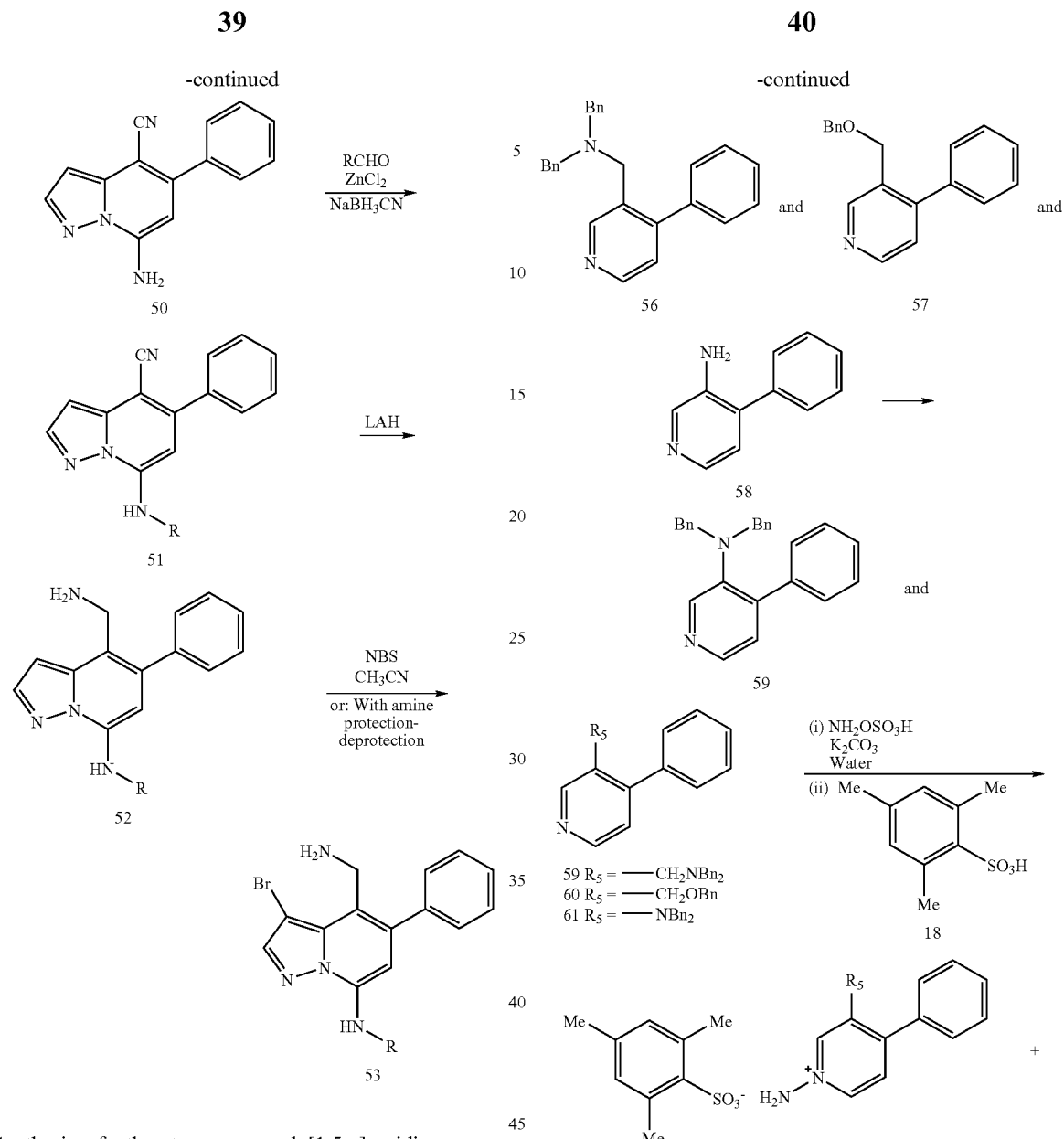
Synthesis of other target pyrazolo[1,5-a]pyridine compounds is illustrated in Scheme 1G.
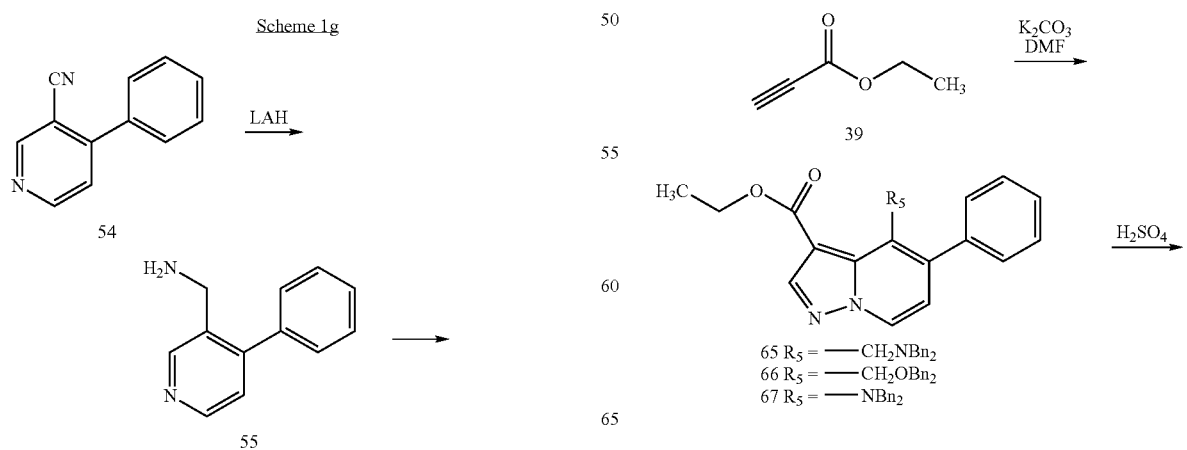

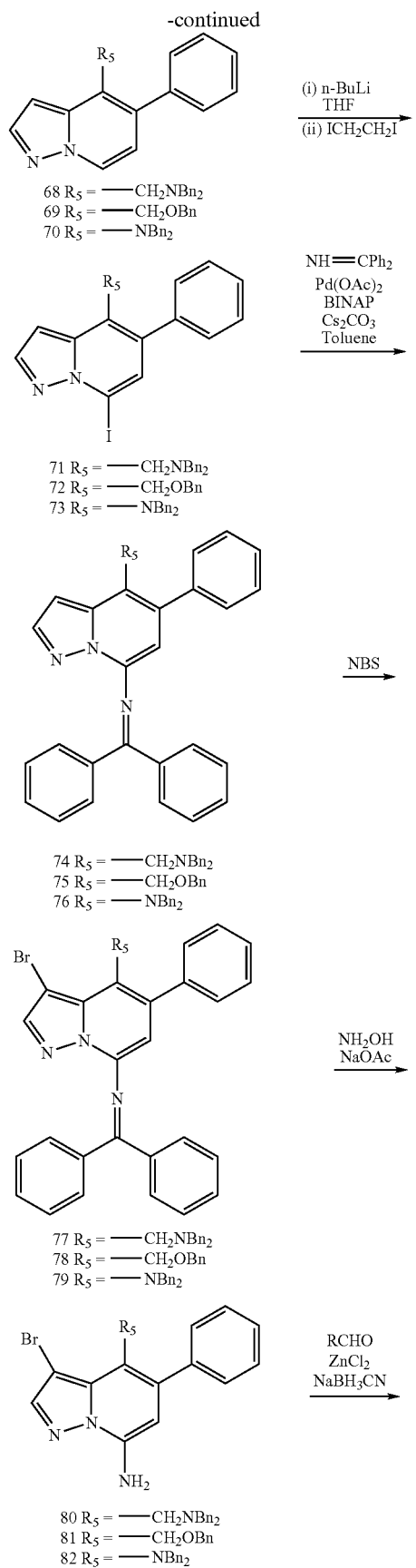

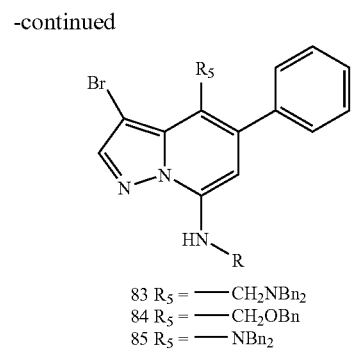

Various benzyl derivatives of the target pyrazolo[1,5-a]pyridine compounds can be prepared by reducing the 3-cyano group of the 3-cyano-4-phenyl pyridine by treating the compound with lithium aluminum hydride forming the methyl amino derivative, which is further derivatized as shown in Scheme 1G then processed using the synthesis described above in Schemes 1b-1d.

A general, synthesis of imidazo[1,2-a]pyridine (Formula V) is described below in Scheme 2.

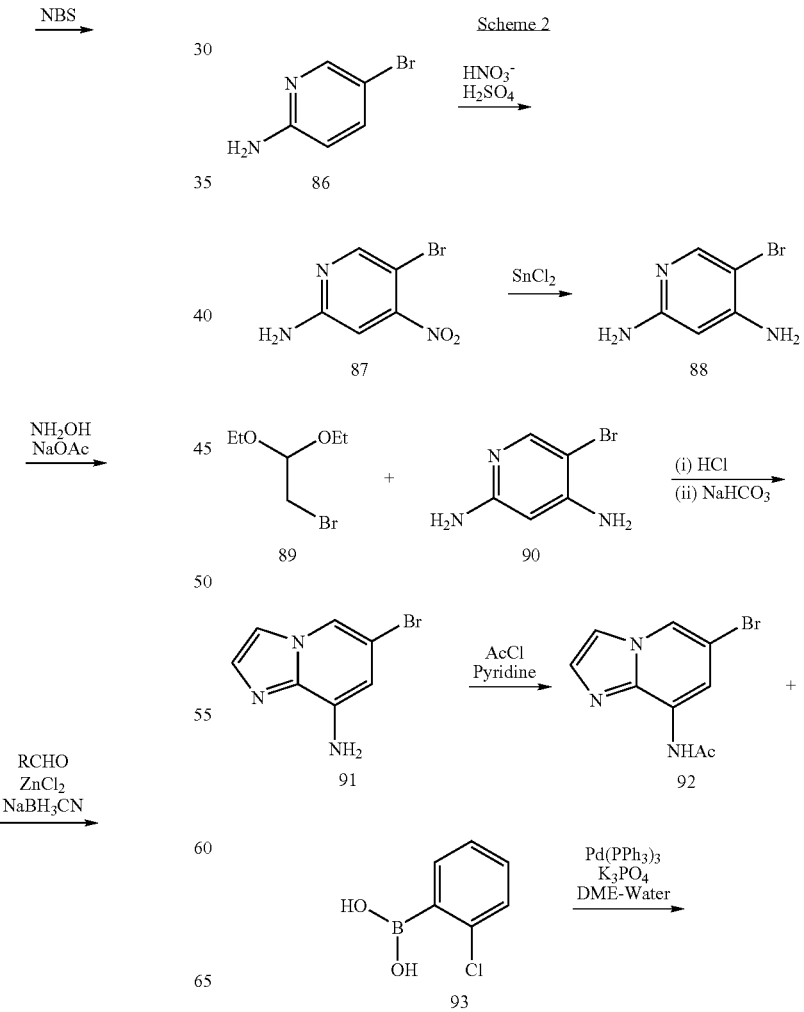

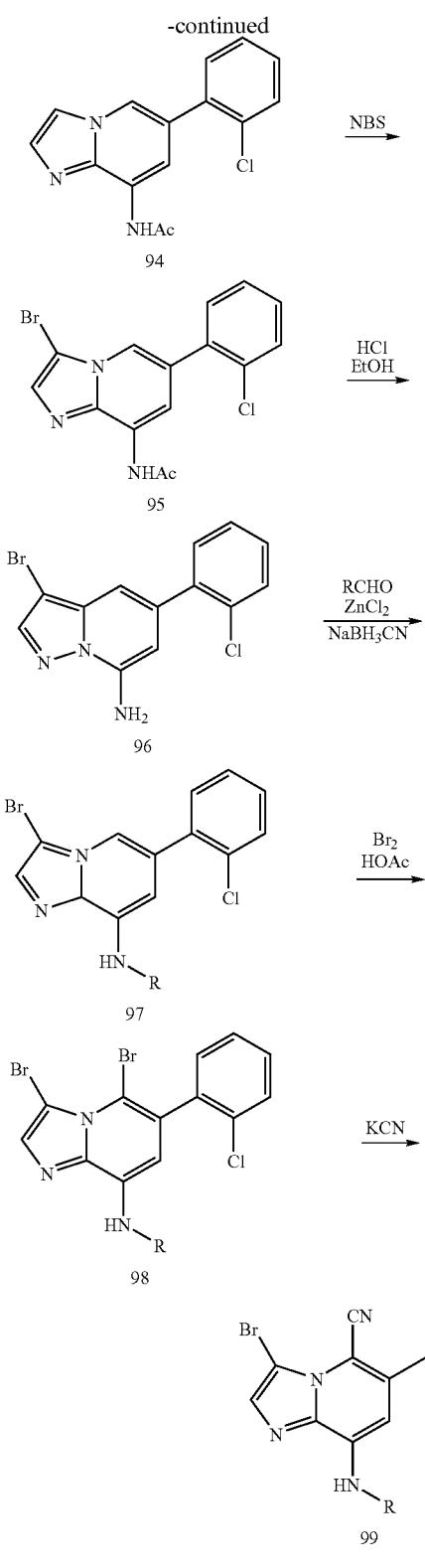

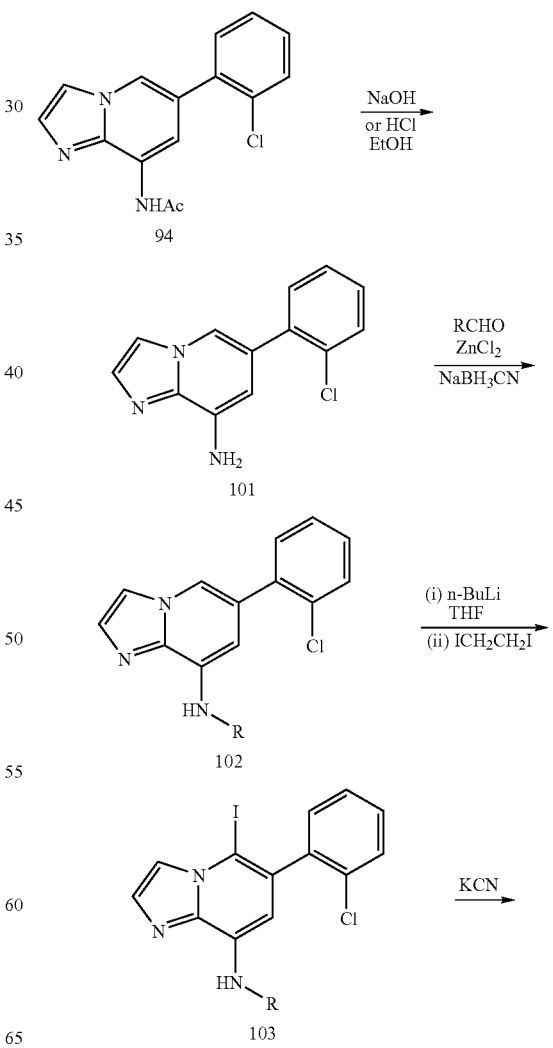

Scheme 2a

6-Bromo-imidazo[1,2-a]pyridin-8-ylamine 91. The amino group is acetylated by treating it with acetyl chloride in the presence of pyridine, which upon addition of the aromatic boronic acid 93 in Pd(PPh$_3$)$_3$, K$_3$PO$_4$, and dimethylether-water furnishes intermediate N-[6-(2-Chloro-phenyl)-imidazo[1,2-a]pyridin-8-yl]-acetamide 94. Treatment of compound 94 with NBS gives rise to intermediate N-[3-Bromo-6-(2-chloro-phenyl)-imidazo[1,2-a]pyridin-8-yl]-acetamide 95, which in the presence of ethanolic hydrochloric acid forms intermediate 3-Bromo-6-(2-chloro-phenyl)-imidazo[1,2-a]pyridin-8-ylamine 96, which reacts with the appropriate aldehyde in zinc chloride and sodium cyanoborohydride to give the desired intermediate amine 97. Treatment with bromine and acetic acid yields the desired 3,5-Dibromo-6-(2-chloro-phenyl)-imidazo[1,2-a]pyridin-8-ylamine derivative 98, which is converted to the target compound 8-Amino-3-bromo-6-(2-chloro-phenyl)-imidazo[1,2-a]pyridine-5-carbonitrile derivative 99.

An alternative route to synthesize the carbonitrile derivative of imidazo[1,2-a]pyridine is illustrated in Scheme 2a.

Treatment of the starting 2-amino-5-bromopyridine 86 with nitric acid and sulfuric acid introduces a nitro group, which is converted to an amine by a reaction with SnCl$_2$. Treatment of this 5-Bromo-4-nitro-pyridin-2-ylamine 90 with 2-Bromo-1,1-diethoxy-ethane 89 in the presence of hydrochloric acid followed by sodium bicarbonate yields

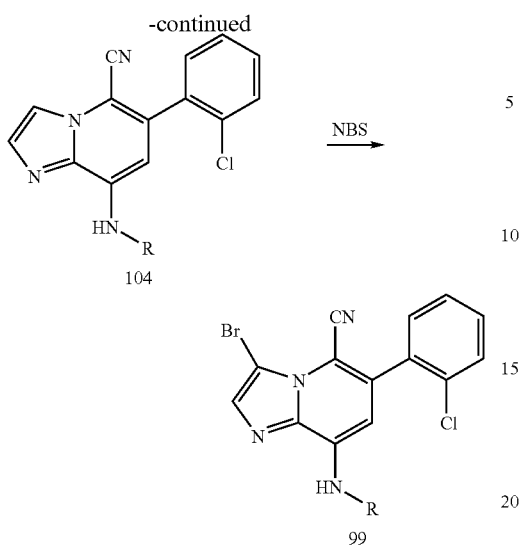

Treatment of intermediate N-[6-(2-Chloro-phenyl)-imidazo[1,2-a]pyridin-8-yl]-acetamide 94 with sodium hydroxide or ethanolic hydrochloric acid converts the acetamide to its amine, which is then treated with an appropriate aldehyde in the presence of zinc chloride and cyanosodiumborohydride giving rise to a derivatized amine intermediate 102. Intermediate 102 is lithiated and iodated at position 5 then treated with potassium cyanide to replace the iodide group with a carbonitrile group in intermediate 104. Treatment of 104 with NBS yields brominated target compound 8-Amino-3-bromo-6-(2-chloro-phenyl)-imidazo[1,2-a]pyridine-5-carbonitrile derivative 99.

A general route to synthesize the amino derivative of imidazo[1,2-a]pyridine is illustrated in Scheme 2b.

Scheme 2b

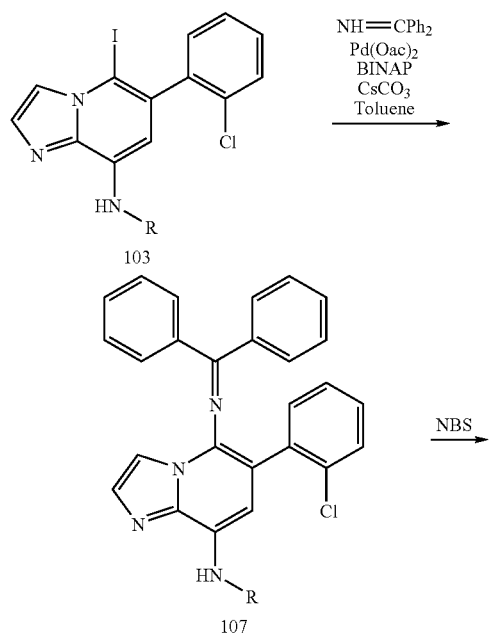

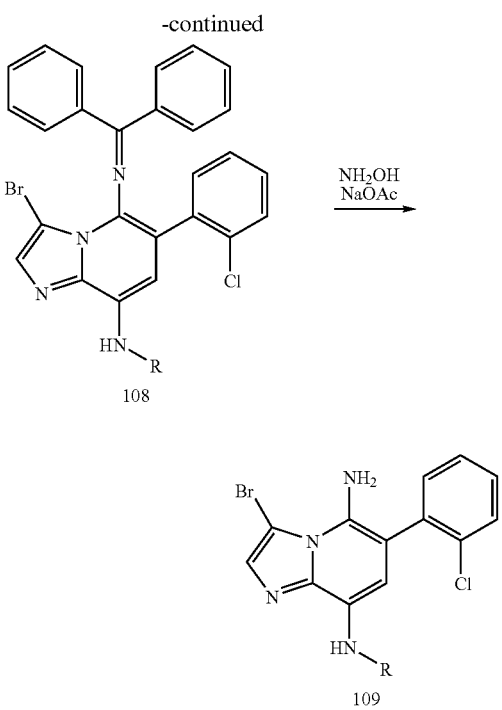

The iodated intermediate 103 is converted to an amine by first treating 103 with benzhydrylideneamine, Pd(OAc)2, (2,2'-bis(diphenylphosphino)-1,1'-binaphthyl) (BINAP), cesium carbonate, and toluene to form intermediate 107, which is then treated with NBS to brominate the imidazo group to form intermediate 108. Intermediate 108 is converted to the amine by treatment with ammonia and sodium acetate to yield the amine derivative of the imidazo[1,2-a]pyridine target compound 109.

A general route to synthesize the methyl amino derivative of imidazo[1,2-a]pyridine is illustrated in Scheme 2c.

Scheme 2c

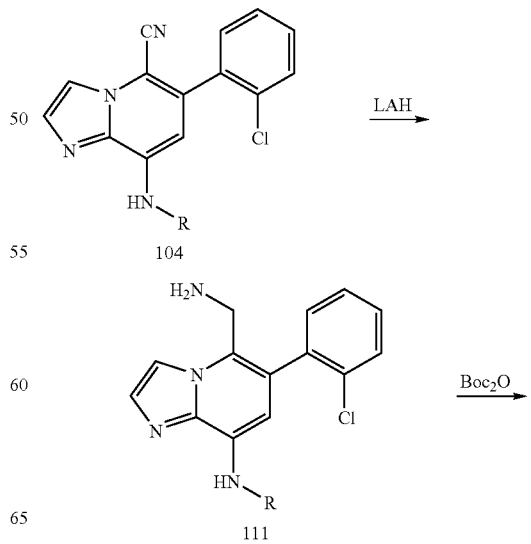

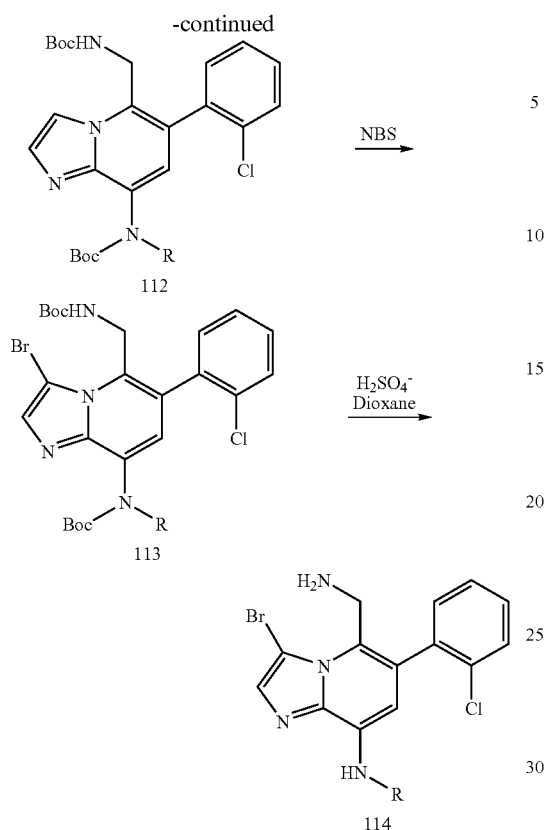

The carbonitrile group of the 8-amino derivative of imidazo[1,2-a]pyridine-5-carbonitrile is reduced to a methylamino group using lithium aluminum hydride to yield intermediate 111. Each of the amino substituents of intermediate 111 are protected with a tertbutyloxycarbonyl (BOC) protection group by a reaction with a BOC anhydride reagent. The imidazo ring of the protected intermediate is brominated with NBS then the compound is deprotected with sulfuric acid in dioxane to yield target compound 5-aminomethyl-3-bromo-6-(2-chloro-phenyl)-imidazo[1,2-a]pyridine-8-ylamine derivative 114.

A general, synthesis of imidazo[1,5-a]pyrazine (Formula VI) is described below in Scheme 3.

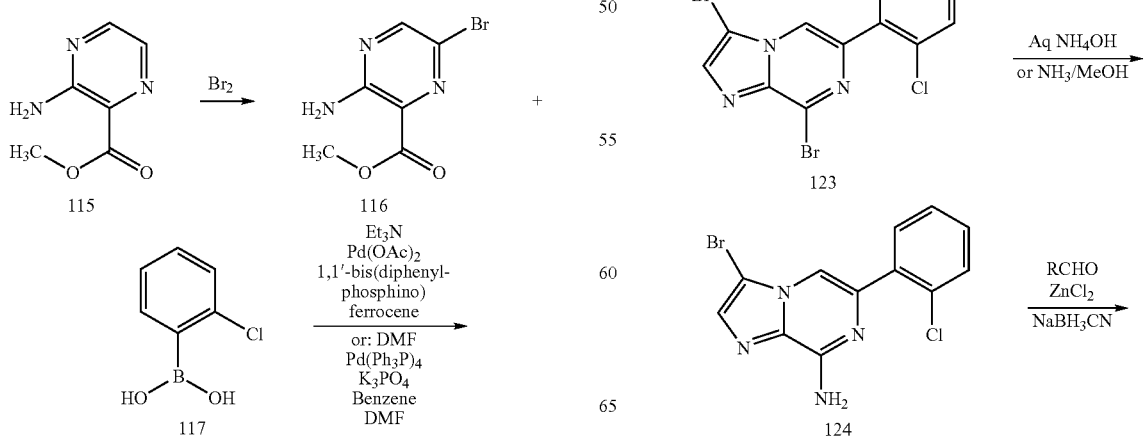

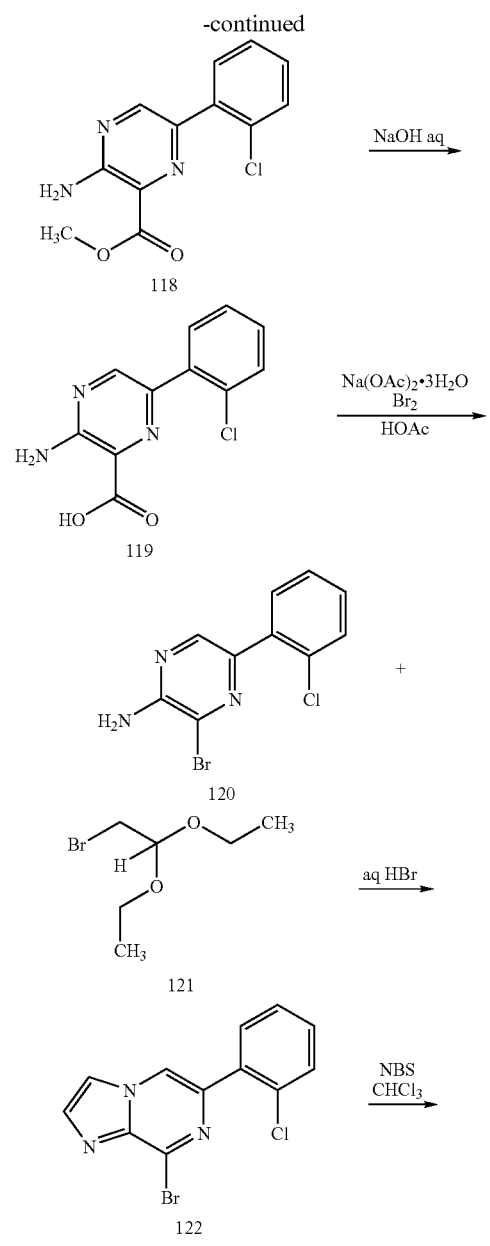

Alternative route to synthesis of intermediate 124 is illustrated in Scheme 3a.

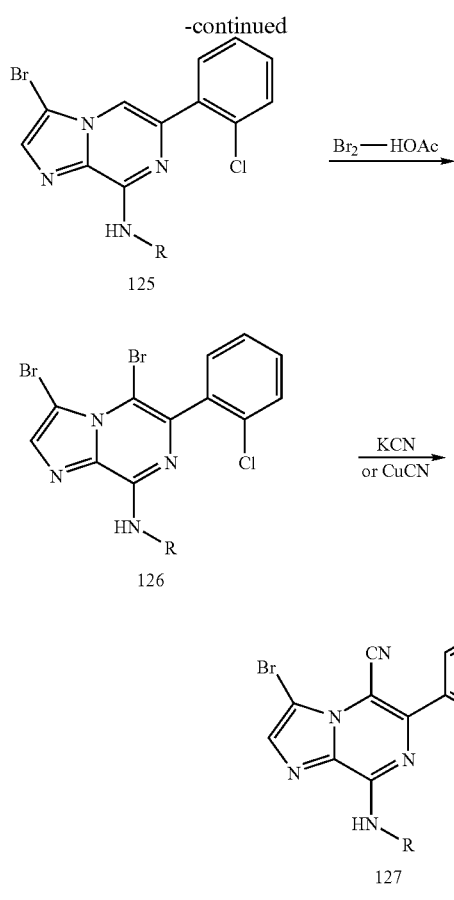

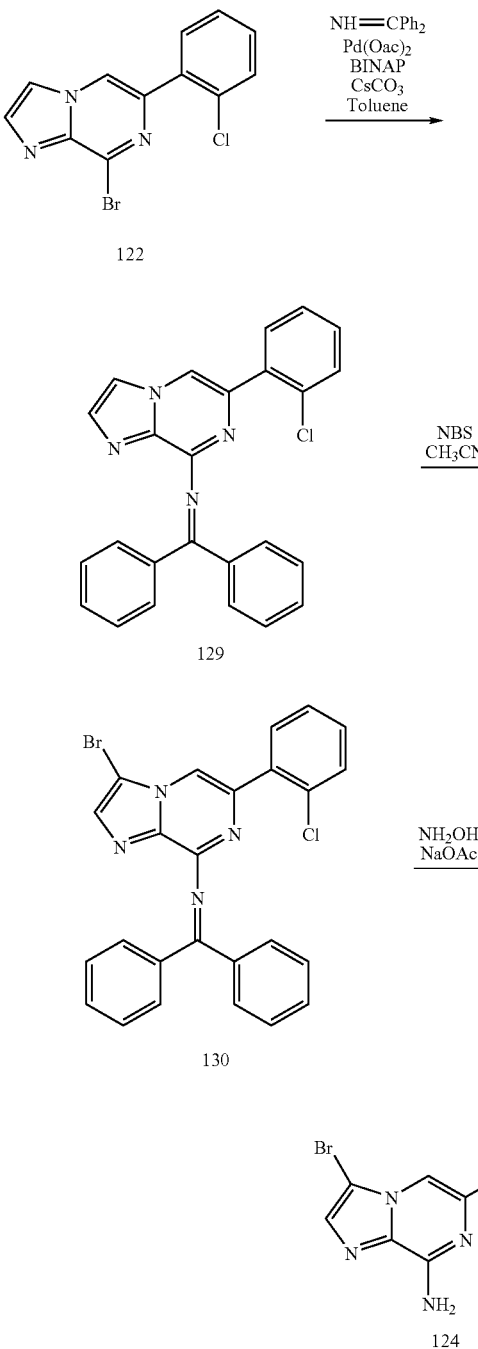

Treatment of the commercially available starting compound 3-amino-pyrazine-2-carboxylic acid methyl ester 115 with bromine provides the 6-bromo derivative of compound 115, which undergoes a Suzuki coupling reaction by treating compound 115 with an aryl boronic acid in the presence of the triethyl amine, palladium diacetate, 1,1-bis(diphenyl-phosphine)ferrocene, dimethyl formamide, palladium tetra triphenyl phosphate, potassium phosphate, and benzene forming 3-amino-6-(2chlorophenyl)-pyrazine-2-carboxylic acid methylester. The methyl ester is hydrolyzed in aqueous sodium hydroxide leaving the carboxylic acid 119, which is replaced by a bromine substituent after treatment with sodium diacetate and bromine in acetic acid it is combined with 2-bromo-1,1-diethoxy-ethane 121 in aqueous hydrobromic acid yielding imidopyrazine 122. The imidazo group is brominated by treatment with NBS in chloroform to yield intermediate 123. Selective replacement of the bromine with an amine occurs by treatment of intermediate 123 with ammonium hydroxide or ammonia in methanol forming intermediate compound 124. Intermediate 124 is reacted with the appropriate aldehyde in the presence of zinc chloride followed by cyano sodium borohydride to give rise to intermediate 3-Bromo-6-(2-chloro-phenyl)-imidazo[1,2-a]pyrazin-8-ylamine derivative 125. Intermediate 125 is further brominated at position 5 by treatment with bromine in acetic acid to provide intermediate 126. Intermediate 126 is converted to target compound 8-Amino derivative-3-bromo-6-(2-chloro-phenyl)-imidazo[1,2-a]pyrazine-5-carbonitrile 127 after treatment with potassium or copper cyanide.

Treatment of compound 122 with benzhydrylideneamine in the presence of palladium diacetate, BINAP, cesium carbonate, and toluene yields intermediate 129, which is brominated at its imidazo ring by treatment with NBS in acetonitrile to yield intermediate 130. Intermediate 130 is aminated by using ammonia in sodium acetate to form intermediate 124.

Route to the amino derivative of imidazo [1,5-a]pyrazine is illustrated in Scheme 3b.

Scheme 3b

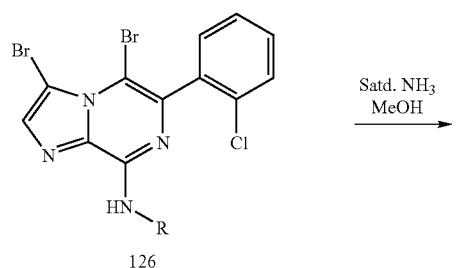

Scheme 4

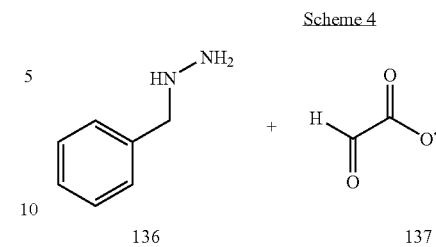

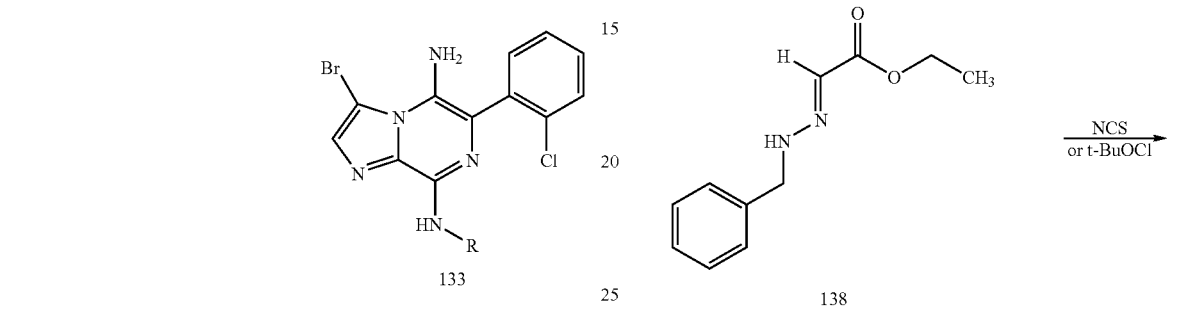

Treatment of intermediate 126 with saturated ammonia in methanol selectively replaces the bromine group of position 5 with an amino group yielding the target amino substituted imidazo [1,5-a]pyrazine.

Route to the methyl amino derivative of imidazo [1,5-a] pyrazine is illustrated in Scheme 3c.

Scheme 3c

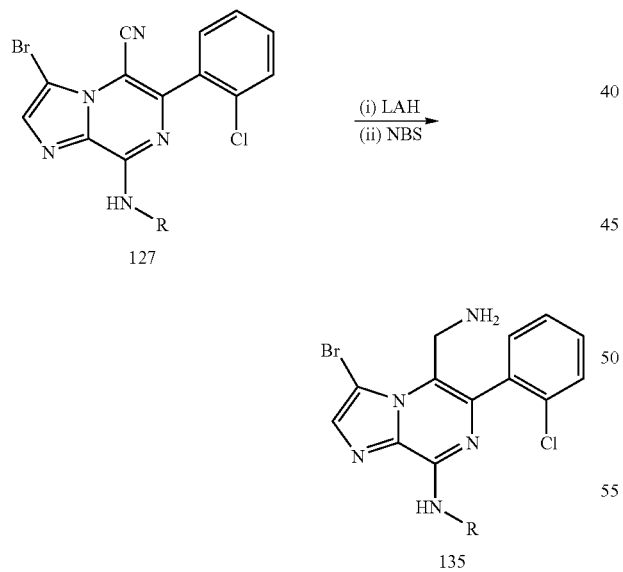

The cyano substituted imidazo [1,5-a]pyrazine 127 is treated with lithium aluminum hydride which reduces both the carbonitrile group to the target methyl amino substituted imidazo [1,5-a]pyrazine and removes the 3-brono groups which is subsequently re-introduced with NBS to afford 135.

A general, synthesis of pyrazolo [1,5-c]pyrimidine (Formula IV) is described below in Scheme 4.

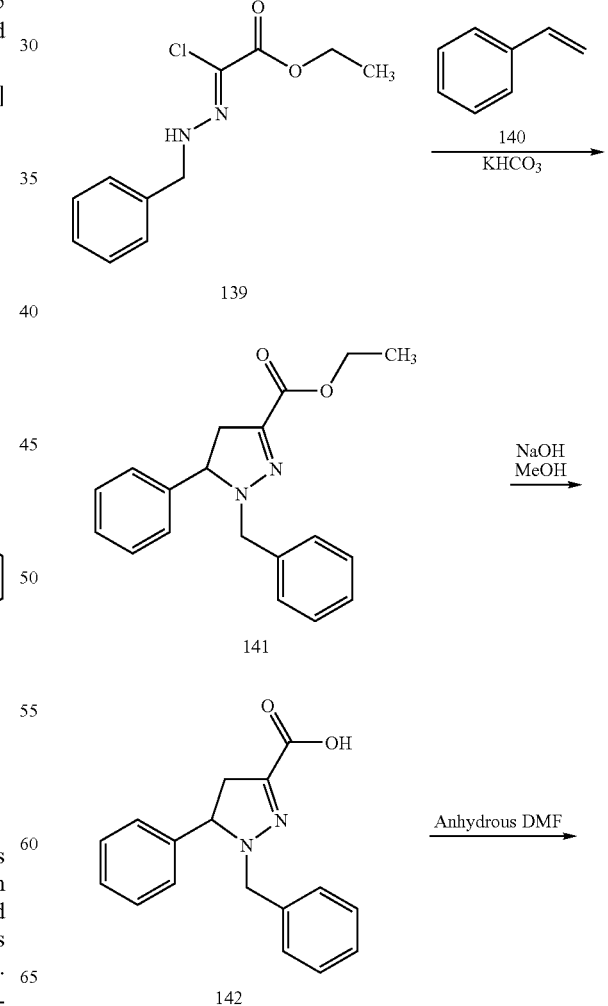

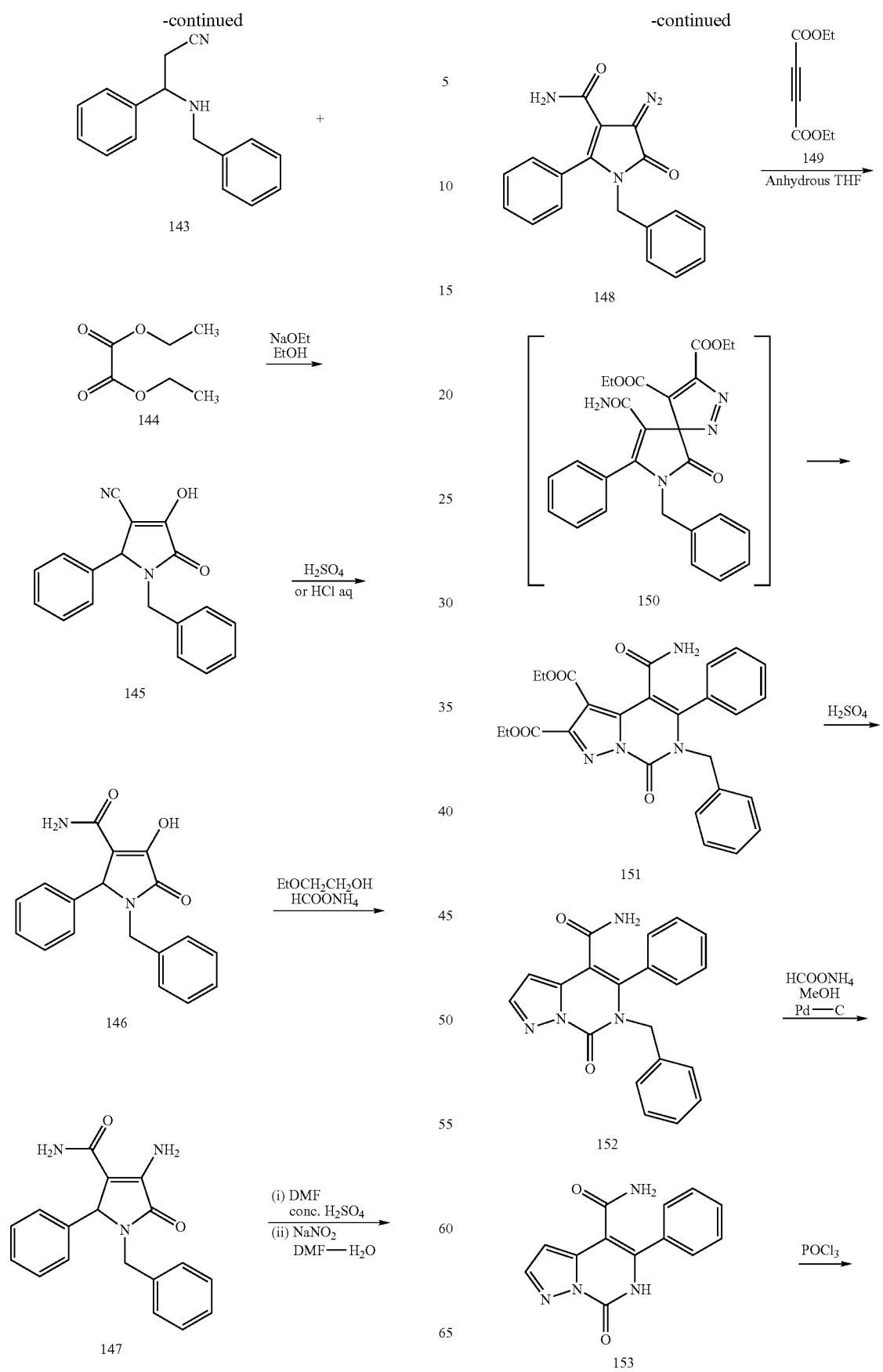

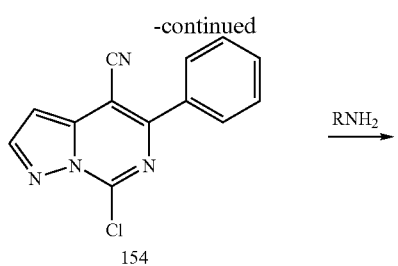

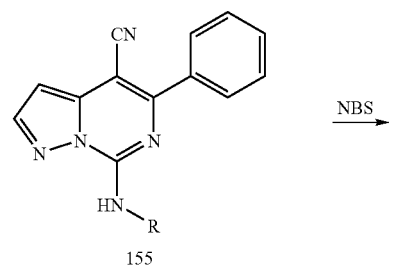

4-carbamoyl-7-oxo-5-phenyl-6,7-dihydro-pyrazolo[1,5-c]pyrimidine-2,3-dicarboxylic acid diethyl ester 151. Reflux of intermediate 151 in the presence of the acid gives rise to intermediate 6-Benzyl-7-oxo-5-phenyl-6,7-dihydro-pyrazolo[1,5-c]pyrimidine-4-carboxylic acid amide 152. Heating formic acid and ammonium ion mixture in methanol and 10% Pd—C to reflux eliminates the benzyl group forming intermediate 7-Oxo-5-phenyl-6,7-dihydro-pyrazolo[1,5-c]pyrimidine-4-carboxylic acid amide 153. Reflux of 153 in phosphorous oxychloride forms intermediate 7-Chloro-5-phenyl-pyrazolo[1,5-c]pyrimidine-4-carbonitrile 154 and treatment with the appropriate amine represented as Y—NH$_2$ results in a substitution of the chloride ion of 154 with the described amine derivative intermediate 155. Treatment of 155 with NBS forms target compound 7-Amino derivative-3-bromo-5-phenyl-pyrazolo[1,5-c]pyrimidine-4-carbonitrile 156.

A route to the synthesis of a methyl amino pyrazolo [1,5-c]pyrimidine is described below in Scheme 4a.

Scheme 4a

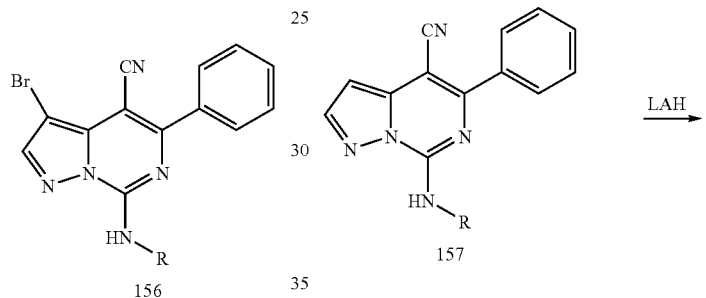

Combination of the starting Benzyl-hydrazine 136 with Oxo-acetic acid ethyl ester 137 gives rise to intermediate (Benzyl-hydrazono)-acetic acid ethyl ester 138, which is chlorinated by treatment with N-chloromethyl succinamide or tertiary butoxy chloride to form intermediate 139. The combination of Intermediate 139 with vinyl benzene 140 forms the ester intermediate 1-Benzyl-5-phenyl-4,5-dihydro-1H-pyrazole-3-carboxylic acid ethyl ester 141. Saponification of the ester intermediate 141 gives rise to intermediate 1-Benzyl-5-phenyl-4,5-dihydro-1H-pyrazole-3-carboxylic acid 142 that gives rise to the cyanoamine intermediate 143 when heated to high temperatures in anhydrous dimethylformamide. Upon further reaction of intermediate 143 with diethyl oxalate 144 affords the intermediate 2,3-dioxo-4-cyanopyrrolidine 145, which forms intermediate 1-Benzyl-4-hydroxy-5-oxo-2-phenyl-2,5-dihydro-1H-pyrrole-3-carboxylic acid amide 146 under acidic conditions and an amino group replaces the OH group forming intermediate 4-Amino-1-benzyl-5-oxo-2-phenyl-2,5-dihydro-1H-pyrrole-3-carboxylic acid amide 147. Treatment of Intermediate 147 with dimethylformamide and sodium nitrite forms intermediate 1-Benzyl-4-imino-5-oxo-2-phenyl-4,5-dihydro-1H-pyrrole-3-carboxylic acid amide 148 and a combination with compound But-2-ynedioic acid diethyl ester 149 forms an intermediate 7-Benzyl-9-carbamoyl-6-oxo-8-phenyl-1,2,7-triaza-spiro[4.4]nona-1,3,8-triene-3,4-dicarboxylic acid diethyl ester 150, which converts to intermediate 6-Benzyl-

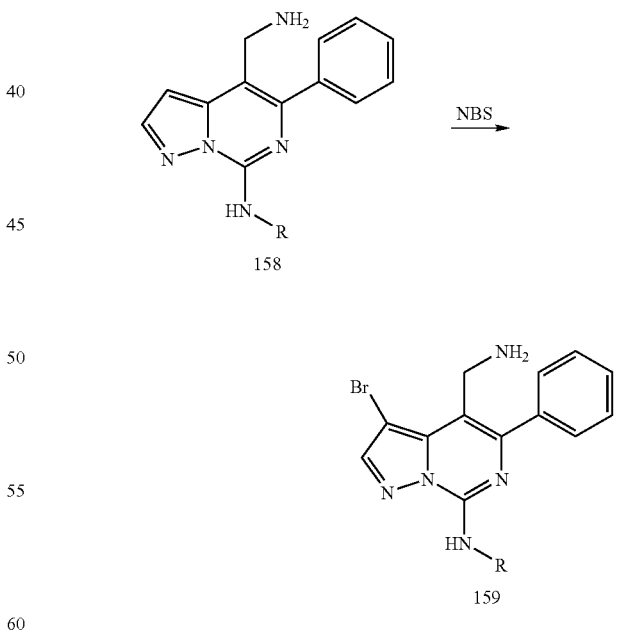

Treatment of intermediate 157 with lithium aluminum hydride followed by NBS forms target compound 4-Aminomethyl-3-bromo-5-phenyl-pyrazolo[1,5-c]pyrimidin-7-ylamine derivative 159.

A general, synthesis of 2H-indazoles (Formula VII) is described below in Scheme 5.

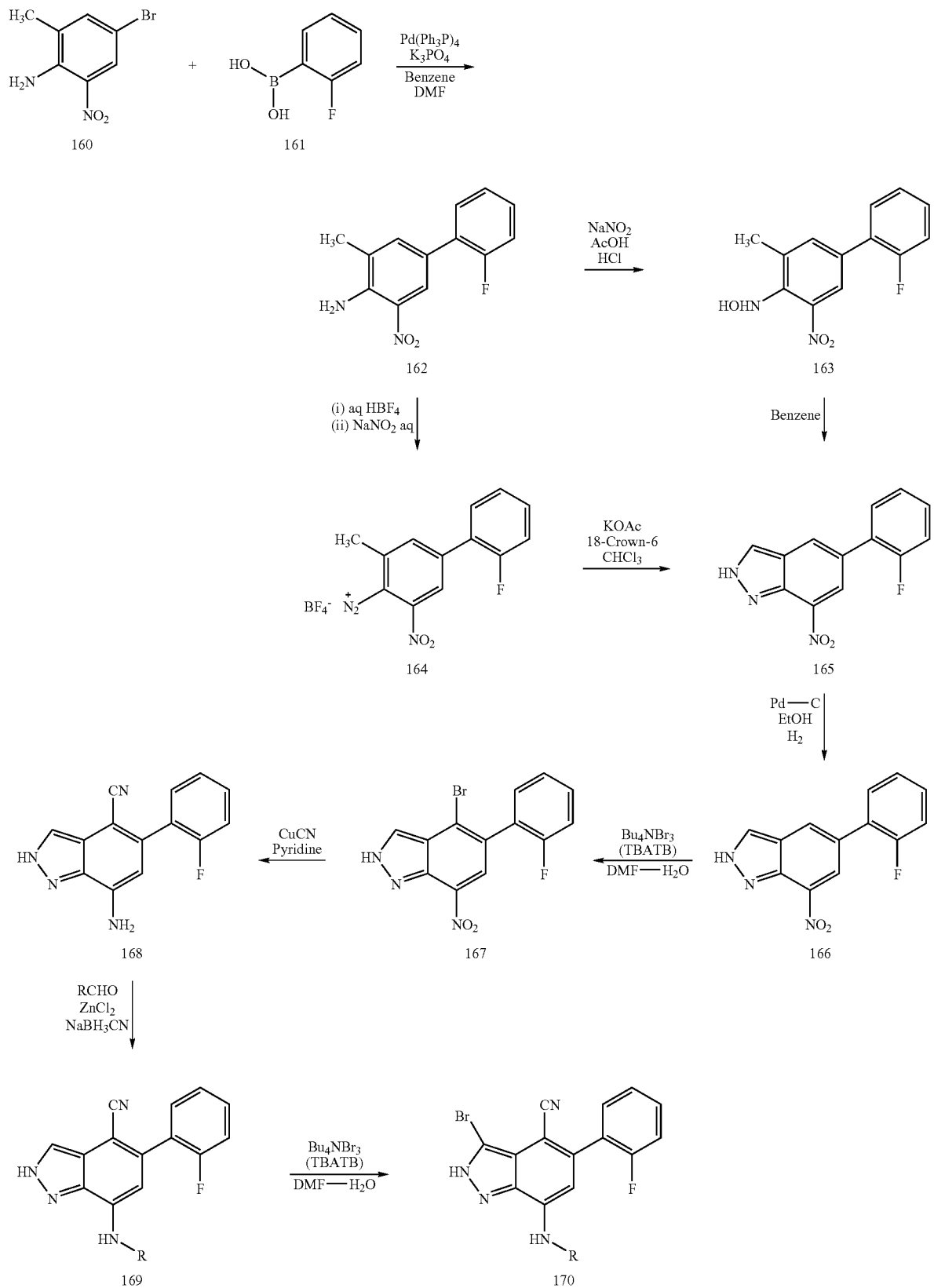

Reflux of a combination of starting compounds 4-Bromo-2-methyl-6-nitro-phenylamine 160 and aromatic boronic acid 161 in the presence of Pd(Ph₃P)₄, K₃PO₄, Benzene, dimethylformamide gives rise to intermediate 2'-Fluoro-5-methyl-3-nitro-biphenyl-4-ylamine 162. Tricyclic intermediate 5-(2-Fluoro-phenyl)-7-nitro-2H-indazole 165 is formed from intermediate 162 by using one of two reactions. One reaction involves treating intermediate 162 with sodium nitrite, acetic acid, and hydrochloric acid to form intermediate N-(2'-Fluoro-5-methyl-3-nitro-biphenyl-4-yl)-hydroxylamine 163 then refluxing intermediate 163 in benzene to form intermediate 165. The second reaction involves treating intermediate 162 with $HBF_4$ and sodium nitrite forming intermediate 2'-Fluoro-5-methyl-3-nitro-biphenyl-4-diazonium$^+$ $BF_4^-$ 164 then treating intermediate 164 with potassium acetate and 18-Crown-6 in chloroform to form intermediate 165. Intermediate 165 is treated with Pd—C in ethanol and hydrogen, which reduces the nitro substituent of intermediate 165 to an amine forming intermediate 5-(2-Fluoro-phenyl)-2H-indazol-7-ylamine 166. Treatment of intermediate 166 with Bu₄NBr₃ (TBATB) and DMF-H₂O brominated intermediate 166 to form intermediate 4-Bromo-5-(2-fluoro-phenyl)-2H-indazol-7-ylamine 167. The bromine of intermediate 167 is replaced with a carbonitrile group by refluxing in coppercyanide in pyridine forming intermediate 7-Amino-5-(2-fluoro-phenyl)-2H-indazole-4-carbonitrile 168. Reductive alkylation of intermediate 168 is accomplished by treating intermediate 168 with the appropriate aldehyde in the presence of zinc chloride and sodium cyano borohydride forming intermediate 169, which is brominated by treatment with Bu₄NBr₃ (TBATB) in DMF-H₂O forming target compound 7-Amino-3-bromo-5-(2-fluoro-phenyl)-2H-indazole-4-carbonitrile derivative 170

Route to the amino methyl 2H-indazole derivative is illustrated in Scheme 5a.

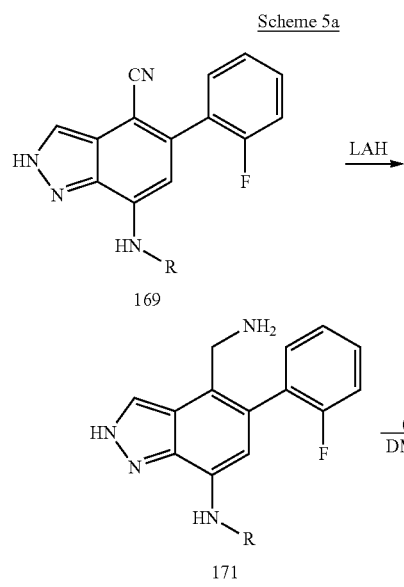

The carbonitrile group of Intermediate 169 is reduced with lithium aluminum hydride yielding the methylamino substituent group of intermediate 171. Intermediate 171 is brominated by treatment with Bu₄NBr₃ (TBATB) and DMF-H₂O to form target compound 4-Aminomethyl-3-bromo-5-(2-fluoro-phenyl)-2H-indazol-7-ylamine 172.

Route to the amino 2H-indazole derivative is illustrated in Scheme 5b.

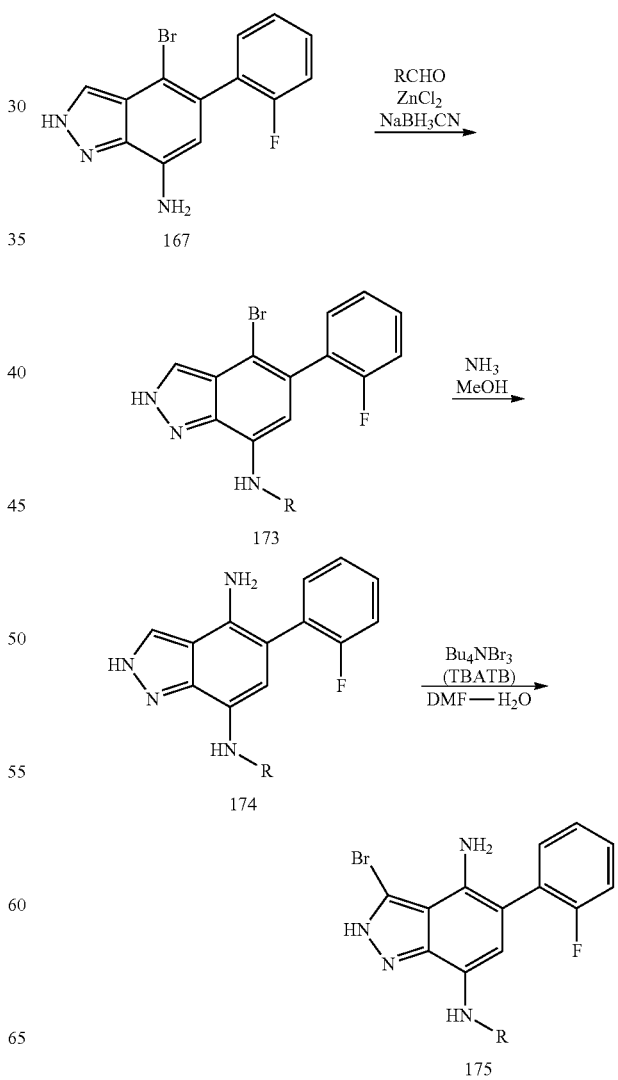

Intermediate 167 undergoes reductive alkylation to form compound intermediate 173. The bromine group is replaced with an amine substituent by refluxing in ammonia and methanol to form intermediate 174. The imidazo ring of intermediate 174 is brominated by treatment with TBATB and dimethylformamide in water to form target compound 3-Bromo-5-(2-fluoro-phenyl)-2H-indazole-4,7-diamine derivative 175.

PREPARATIVE EXAMPLES

Preparative Example 1

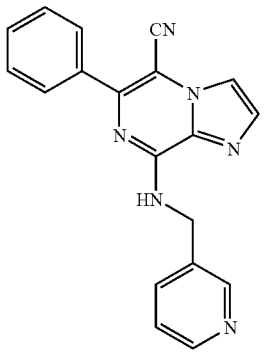

Step A

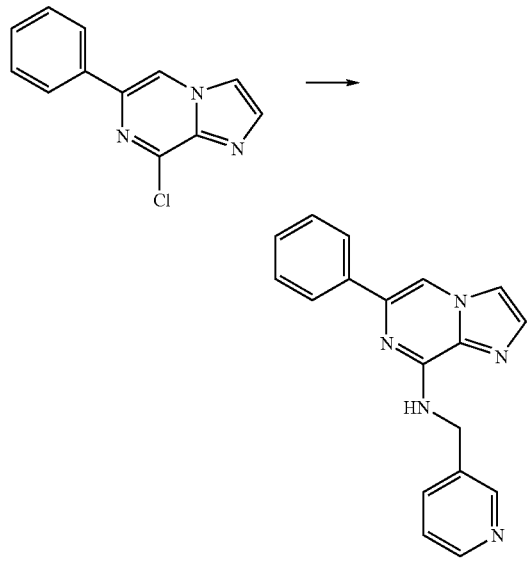

A mixture of the starting material prepared as in WO2004/026877 (640 mg, 2.78 mmol), 3-(aminomethyl)pyridine (360 mg, 3.34 mmol), diisopropylethylamine (3.2 mL), and anhydrous dioxane (8 mL) was stirred at 90° C. under $N_2$ for 72 hr. The solvent was evaporated and the residue was purified by column chromatography on silica gel with $CH_2Cl_2$/7N $NH_3$ in MeOH (40:1). White solid (720 mg, 86%) was obtained. LCMS: MH$^+$=302.

Step B

A solution of N-bromosuccinimide ("NBS") (424 mg, 2.36 mmol) in anhydrous $CH_3CN$ (20 mL) was added under $N_2$ to a stirred solution of the product of Step A (710 mg, 2.36 mmol) in anhydrous $CH_3CN$ (20 mL) and $CH_2Cl_2$ (20 mL). The mixture was stirred at 25° C. for 2 hr and the solvent was then evaporated. Chromatography on silica gel with EtOAc/MeOH (20:1) afforded a white solid (710 mg, 79%). LCMS: M$^+$=380, M.P.=169-170° C.

Step C

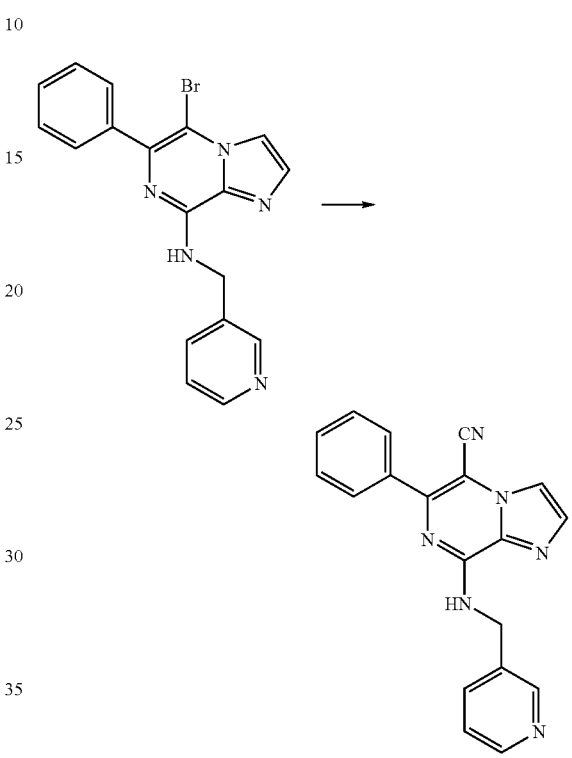

A mixture of the product from Step B (500 mg, 1.31 mmol), $Zn(CN)_2$ (300 mg, 2.56 mmol), tris(dibenzylideneacetone)dipalladium (150 mg, 0.16 mmol), and bis(tri-t-butylphosphine)palladium (150 mg, 0.29 mmol) in anhydrous DMF (10 mL) was stirred at 140° C. under $N_2$ for 20 hr. The solvent was evaporated and the residue was purified by column chromatography and then by preparative TLC on silica gel with $PhCH_3$/MeOH (10:1). A Pale orange solid (9 mg, 2%) was obtained. LCMS: MH$^+$=327.

Preparative Example 2

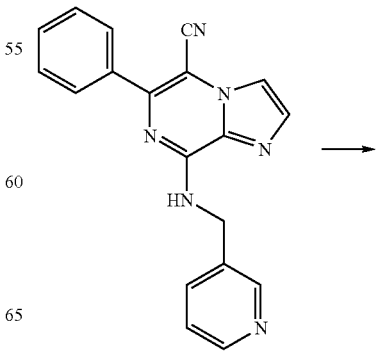

-continued

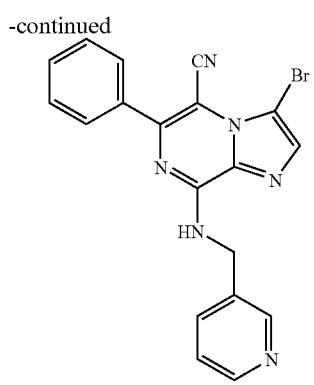

A solution of N-bromosuccinimide ("NBS") (2.7 mg, 0.015 mmol) in anhydrous $CH_3CN$ (0.2 mL) was added under $N_2$ to a stirred solution of the product from Preparative Example 1, Step C (5.0 mg, 0.015 mmol) in anhydrous $CH_3CN$ (0.5 mL). The mixture was stirred at 25° C. for 24 hr and the solvent was then evaporated. Chromatography on silica gel with $PhCH_3$/MeOH (7:1) afforded a colorless solid (3 mg, 48%). LCMS: $M^+$=405.

Preparative Example 3

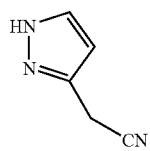

Step A

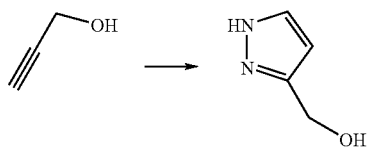

Propargyl alcohol (10.0 g, 78 mM) was added under argon to a stirred solution of 2.0 M Trimethylsilyl diazomethane in hexanes (89 mL, 178 mM) in anhydrous $Et_2O$ (200 mL). The solution stirred for 11 days at 25° C. and the solvent then evaporated. Chromatography on silica gel (30×5 cm) with $CH_2Cl_2$/MeOH (10:1) afforded the product (3.15 g, 18%). (Jones, Reuben, JACS, 71, 3994-4000. 1949)

Step B

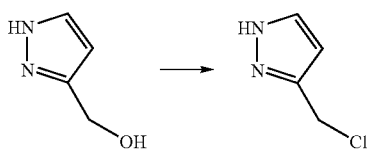

$SOCl_2$ (3.45 mL, 47.3 mM) was added to a vigorously stirring biphasic mixture of (1H-Pyrazol-3-yl)-methanol (2.59 g, 26.4 mM) from Step A in anhydrous $CH_2Cl_2$ at 0° C. The mixture was stirred at 0° C. for 0.5 hr and then the solvent and excess $SOCl_2$ were evaporated, forming 3-Chloromethyl-1H-pyrazole. The 3-Chloromethyl-1H-pyrazole was used without purification for Step C. (Jones, Reuben, JACS, 71, 3994-400, 1949)

Step C

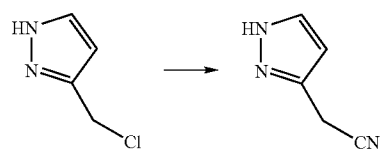

To a stirred solution of KCN (15.86 g, 243 mM) in $H_2O$ (30 mL) at 0° C. was added dropwise over 0.33 hr, a solution of 3-Chloromethyl-1H-pyrazole (3.08 g, 26.4 mM) from Step B in absolute EtOH (62 mL). After 2.5 hours, the reaction mixture was filtered, the solids were washed with absolute EtOH (2×50 mL), and the filtrate was evaporated. Chromatography on silica gel (30×5 cm) with $CH_2Cl_2$/MeOH (97.5:2.5) afforded (1H-Pyrazol-3-yl)-acetonitrile (1.93 g, 68%). (Jones, Reuben, JACS, 71, 3994-4000, 1949)

Preparative Example 4

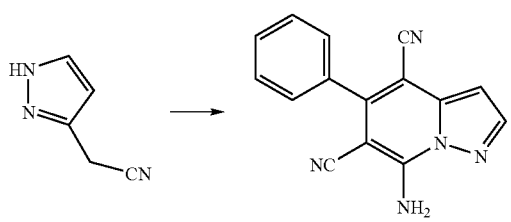

To a stirred solution of (1H-Pyrazol-3-yl)-acetonitrile (100 mg, 0.93 mM) from Step C of Preparative Example 3, in absolute EtOH (4.7 mL) at 25° C. was added benzylidene malononitrile (144 mg, 0.93 mM) and piperidine (0.009 mL, 0.09 mM). The mixture then refluxed for 1.0 hr. The solvent evaporated. Chromatography on silica gel (60×2.5 cm) with $CH_2Cl_2$ afforded 7-Amino-5-phenyl-pyrazolo[1,5-a]pyridine-4,6-dicarbonitrile (34.6 mg, 14%) LCMS: $MH^+$=260; HRMS: m/z 260.0938 ($MH^+$), Calcd. $C_{15}H_9N_5$: m/z 260.0936; $\delta_C$ (DMSO) CH: 99.0, 128.5, 128.5, 128.8, 128.8, 129.8, 145.4; C: 75.4, 86.9, 115.5, 116.0, 134.8, 138.9, 148.1, 149.4.

Preparative Example 5

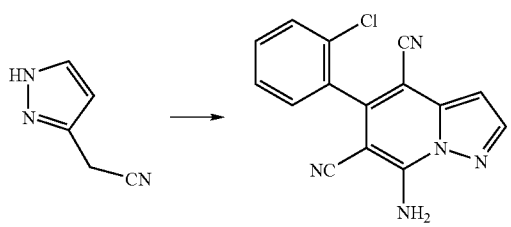

To a stirred solution of (1H-Pyrazol-3-yl)-acetonitrile (1.56 g, 14.5 mM) from Preparative Example 3 Step C in absolute EtOH (73 mL) at 25° C. was added o-chlorobenzylidene malononitrile (2.74 g, 14.5 mM) and piperidine (0.14 mL, 1.45 mM). The mixture then refluxed for 1.75 hr. The solvent evaporated. Chromatography on silica gel (30×5 cm) with $CH_2Cl_2$ afforded 7-Amino-5-(2-chloro-phenyl)-pyrazolo[1,5-a]pyridine-4,6-dicarbonitrile (0.62 g, 15%).

HRMS: m/z 293.0472 (M+), Calcd. $C_{15}H_8N_5Cl_1$: m/z 293.0468; $\delta_C$ (CDCl$_3$) CH: 99.3, 127.6, 129.6, 130.8, 131.6, 145.5; C: 75.7, 86.9, 114.8, 115.1, 131.5, 133.8, 138.4, 145.6, 149.2.

Preparative Example 6

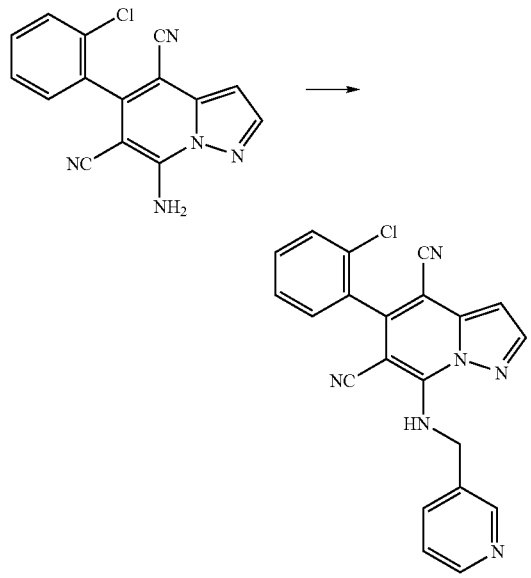

NaH (52 mg, 2 mM) was added to a stirred solution of 7-Amino-5-(2-chloro-phenyl)-pyrazolo[1,5-a]pyridine-4,6-dicarbonitrile (0.30 g, 1 mM) from Preparative Example 5 in anhydrous DMF (6 mL) at 25° C. After 0.5 hr, 3-Picolinyl chloride hydrochloride (167 mg, 1 mM) was added. The mixture was stirred at 25° C. for 0.5 hr and then at 60° C. for 17 hr. The mixture was added to CH$_2$Cl$_2$ (400 mL) and washed with saturated NaHCO$_3$ (60 mL). Chromatography on silica gel (15×5 cm) afforded unreacted starting material (121 mg, 41%) and 5-(2-Chloro-phenyl)-7-[(pyridin-3-ylmethyl)-amino]-pyrazolo[1,5-a]pyridine-4,6-dicarbonitrile 147 mg, 37%). LCMS: MH+=385; HRMS: m/z 385.0967 (MH+) Calcd. $C_{21}H_{14}N_6Cl_1$: m/z 385.0968; $\delta_C$ (CDCl$_3$) CH$_2$: 45.5; CH: 100.8, 124.1, 127.5, 130.3, 130.5, 131.7, 135.7, 144.8, 149.4, 150.2; C: 76.6, 91.7, 114.5, 115.8, 133.0, 133.5, 138.4, 146.5, 146.7.

Preparative Example 7

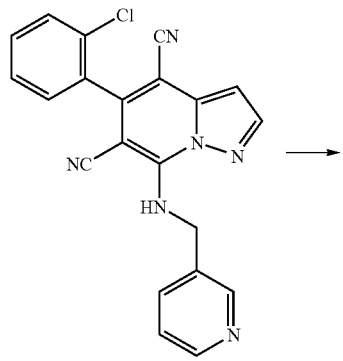

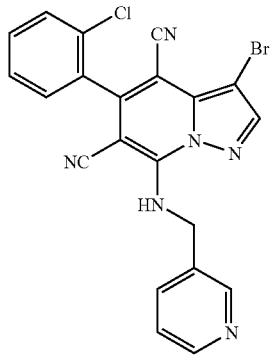

N-Bromosuccinimde (64 mg, 0.34 mM) was added to a stirred solution of Preparative Example 6, 5-(2-Chloro-phenyl)-7-[(pyridin-3-ylmethyl)-amino]-pyrazolo[1,5-a]pyridine-4,6-dicarbonitrile, (140 mg, 0.34 mM) in anhydrous CH$_2$Cl$_2$ (7 mL) and CH$_3$CN (7 mL) at 25° C. The mixture stirred at 25° C. for 90 hr. The mixture was filtered through a medium sintered glass filter and the solid washed with CH$_2$Cl$_2$ (3×25 mL). The filtrate was evaporated and the residue was chromatographed on silica gel (15×2.5 cm) with CH$_2$Cl$_2$ and then a 0.5% solution of (10% NH$_4$OH in MeOH) in CH$_2$Cl$_2$ to afford crude 3-Bromo-5-(2-chloro-phenyl)-7-[(pyridin-3-ylmethyl)-amino]-pyrazolo[1,5-a]pyridine-4,6-dicarbonitrile (59.5 mgs). This sample was further purified by a CH$_2$Cl$_2$/saturated aq. NaHCO$_3$ extraction and chromatographed on silica gel (15×2 cm) with 0.5% solution of (10% NH$_4$OH in MeOH) in CH$_2$Cl$_2$, followed by an Et$_2$O/H$_2$O extraction, and finally a Prep TLC on four 20×20 cm 250 micron silica gel plates developed in 2.0% solution of (10% NH$_4$OH in MeOH) in CH$_2$Cl$_2$. This afforded 3-Bromo-5-(2-chloro-phenyl)-7-[(pyridin-3-ylmethyl)-amino]-pyrazolo[1,5-a]pyridine-4,6-dicarbonitrile. LCMS: MH+=465; $\delta_C$ (DMSO) CH$_2$: 43.7; CH: 123.5, 127.6, 129.6, 130.7, 131.7, 134.8, 145.6, 147.7, 148.0; C: 75.9, 86.3, 87.7, 113.4, 115.6, 131.5, 133.3, 133.7, 147.0, 148.6.

Example 1

Step A

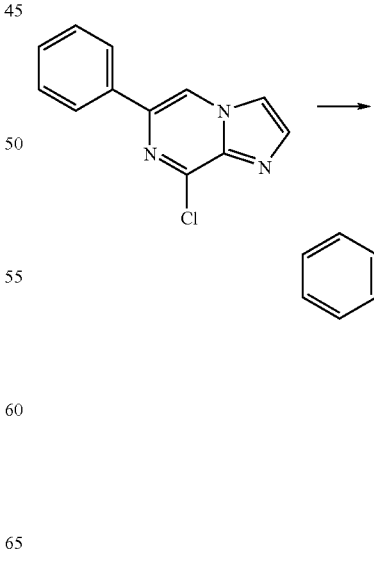

A mixture of the starting material prepared as in WO2004/026877 (640 mg, 2.78 mmol), 3-(aminomethyl)pyridine (360 mg, 3.34 mmol), diisopropylethylamine (3.2 mL), and anhydrous dioxane (8 mL) was stirred at 90° C. under $N_2$ for 72 hr. The solvent was evaporated and the residue was purified by column chromatography on silica gel with $CH_2Cl_2$/7N $NH_3$ in MeOH (40:1). White solid (720 mg, 86%) was obtained. LCMS: $MH^+$=302.

Step B

A solution of N-bromosuccinimide ("NBS") (424 mg, 2.36 mmol) in anhydrous $CH_3CN$ (20 mL) was added under $N_2$ to a stirred solution of the starting material from Step A (710 mg, 2.36 mmol) in anhydrous $CH_3CN$ (20 mL) and $CH_2Cl_2$ (20 mL). The mixture was stirred at 25° C. for 2 hr and the solvent was then evaporated. Chromatography on silica gel with EtOAc/MeOH (20:1) afforded white solid (710 mg, 79%). LCMS: $M^+$=380, M.P.=169-170° C.

Step C

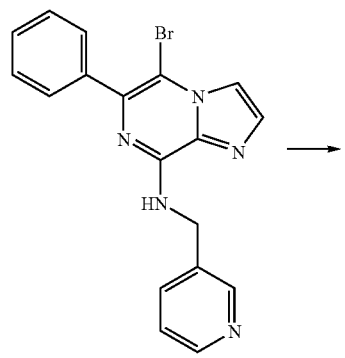

-continued

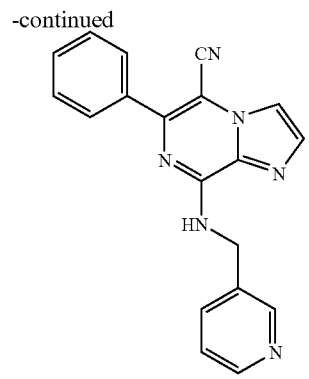

A mixture of the product from Step B (500 mg, 1.31 mmol), $Zn(CN)_2$ (300 mg, 2.56 mmol), tris(dibenzylideneacetone)dipalladium (150 mg, 0.16 mmol), and bis(tri-t-butylphosphine)palladium (150 mg, 0.29 mmol) in anhydrous DMF (10 mL) was stirred at 140° C. under $N_2$ for 20 hr. The solvent was evaporated and the residue was purified by column chromatography and then by preparative TLC on silica gel with $PhCH_3$/MeOH (10:1). Pale orange solid (9 mg, 2%) was obtained. LCMS: $MH^+$=327.

Examples 2-6

The compounds of column 4 shown in Table 2 are prepared by essentially the same procedure set forth in Example 1, only substituting the compound shown in Column 2 and the amine shown in column 3. The cyano substituent of the products shown in column 4 are reduced to a methylamino group as shown in column 5 using lithium aluminum anhydride as illustrated in scheme 1f above. Example 6 is the product of Example 1 that also has been reduced in lithium aluminum anhydride.

TABLE 2

| Example | Column 2 | Column 3 | Column 4 | Column 5 |
|---------|----------|----------|----------|----------|
| 2 | | | | |

TABLE 2-continued

| Example | Column 2 | Column 3 | Column 4 | Column 5 |
|---------|----------|----------|----------|----------|
| 3 | | | | |
| 4 | | | | |
| 5 | | | | |
| 6 | | | | |

Example 7

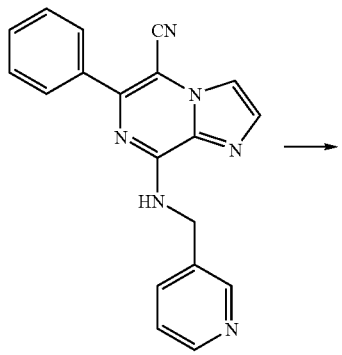

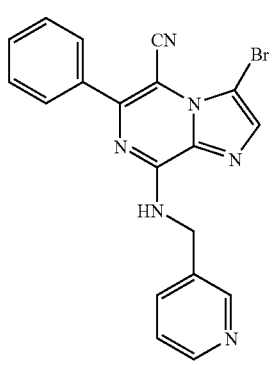

A solution of N-bromosuccinimide ("NBS") (2.7 mg, 0.015 mmol) in anhydrous CH$_3$CN (0.2 mL) was added under N$_2$ to a stirred solution of the product from Preparative Example 1, Step C (5.0 mg, 0.015 mmol) in anhydrous CH$_3$CN (0.5 mL). The mixture was stirred at 25° C. for 24 hr and the solvent was then evaporated. Chromatography on silica gel with PhCH$_3$/MeOH (7:1) afforded a colorless solid (3 mg, 48%). LCMS: M$^+$=405.

Examples 8-11

The compounds of column 3 shown in Table 3 are prepared by essentially the same procedure set forth in Example 7, only substituting the compound shown in Column 2. Again, the cyano substituent of the products shown in column 3 are reduced to a methylamino group as shown in column 4 using lithium aluminum anhydride as illustrated in scheme 1f above. Example 11 is the methylamino substituted version of Example 7 above:

TABLE 3

| Examples | Column 2 | Column 3 | Column 4 |
|---|---|---|---|
| 8 | | | |
| 9 | | | |

TABLE 3-continued

| Examples | Column 2 | Column 3 | Column 4 |
|---|---|---|---|
| 10 | | | |
| 11 | | | |

Example 12

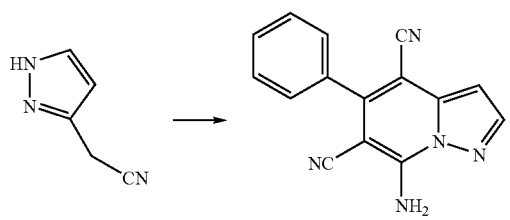

To a stirred solution of (1H-Pyrazol-3-yl)-acetonitrile (100 mg, 0.93 mM) in absolute EtOH (4.7 mL) at 25° C. was added benzylidene malononitrile (144 mg, 0.93 mM) and piperidine (0.009 mL, 0.09 mM). The mixture then refluxed for 1.0 hr. The solvent evaporated. Chromatography done on silica gel (60×2.5 cm) with $CH_2Cl_2$ afforded 7-Amino-5-phenyl-pyrazolo[1,5-a]pyridine-4,6-dicarbonitrile (34.6 mg, 14%) LCMS: $MH^+$=260; HRMS: m/z 260.0938 ($MH^+$), Calcd. $C_{15}H_9N_5$: m/z 260.0936; $\delta_C$ (DMSO) CH: 99.0, 128.5, 128.5, 128.8, 128.8, 129.8, 145.4; C: 75.4, 86.9, 115.5, 116.0, 134.8, 138.9, 148.1, 149.4.

Example 13

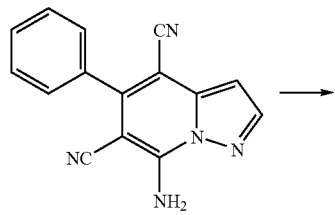

-continued

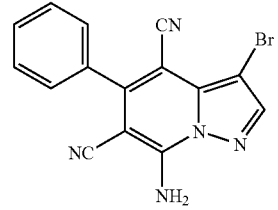

Boc-anhydride and NaOH was added to the product of Example 12 in order to protect its amine as an N-Boc derivative. A solution of N-bromosuccinimide ("NBS") in anhydrous $CH_3CN$ is added and stirred under $N_2$ in anhydrous $CH_3CN$. The mixture is stirred at 25° C. for 24 hr and the solvent is then evaporated. The Boc group may be removed from the amine by stirring with sulfuric acid in dioxane to yield the product 7-Amino-5-phenyl-pyrazolo[1,5-a]pyridine-4,6-dicarbonitrile.

Examples 14-20

The free amine of the product of Example 13 is stirred in the presence of $ZnCl_2$ and $NaBH_3CN$ with the appropriate aldehyde as shown in Column 2 of Table 4 below to produce the various amino derivatives illustrated in column 3:

TABLE 4

| Examples: | Column 2 | Column 3 |
|---|---|---|
| 14 | isobutyraldehyde | pyrazolopyridine with isopropylamino |
| 15 | phenylacetaldehyde | pyrazolopyridine with benzylamino |
| 16 | benzaldehyde | pyrazolopyridine with phenylamino |
| 17 | 3-pyridylacetaldehyde | pyrazolopyridine with (pyridin-3-ylmethyl)amino |
| 18 | nicotinaldehyde | pyrazolopyridine with pyridin-3-ylamino |

TABLE 4-continued

| Examples: | Column 2 | Column 3 |
|---|---|---|
| 19 | 3-hydroxypropanal | pyrazolopyridine with 2-hydroxyethylamino |
| 20 | 2-(piperidin-3-yl)acetaldehyde | pyrazolopyridine with (piperidin-3-ylmethyl)amino |

Example 21-27

The amine derivatives of the compounds of this invention are prepared by following a series of reactions in the order described below. The starting material is the same as that of Scheme 2 above (compound 86). The series of reactions illustrated in Scheme 2 from compound 86 to compound 94 are followed. Next, compound 94 is used according to the series of reactions illustrated in Scheme 2a, beginning with compound 94 to compound 103. Finally, compound 103 is used according to the series of reactions illustrated in Scheme 2b. The series of reactions of Scheme 2b are also illustrated and described below:

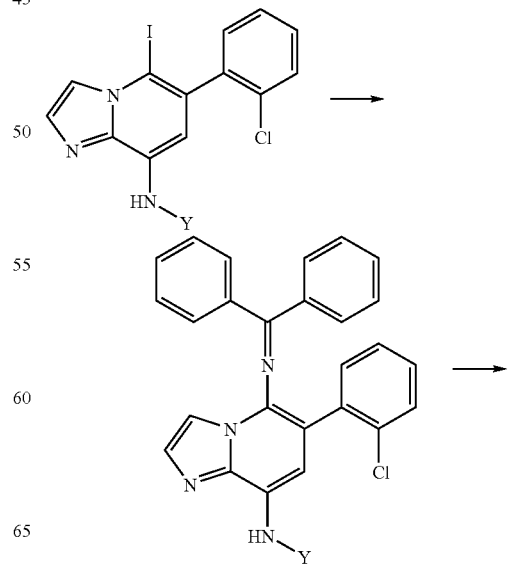

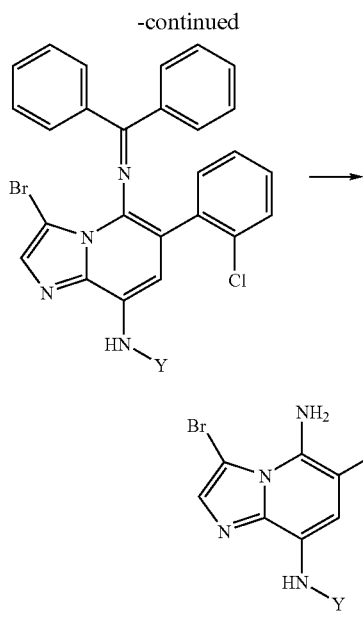

The iodated intermediate is converted to an amine by first treating it with benzhydrylideneamine, Pd(OAc)2, (2,2'-bis(diphenylphosphino)-1,1'-binaphthyl) (BINAP), cesium carbonate, and toluene to form the 5,8-diamine intermediate, which is then treated with NBS to brominate the imidazo group. The brominated 5,8-diamine intermediate is converted to the amine by treatment with NH$_2$OH and NaOAc to yield the amine derivative of the imidazo[1,2-a]pyridine target compounds.

Alternatively, the amine derivatives are formed by following essentially the same procedure described in Scheme 3b wherein intermediates that correspond to intermediate 126 for each compound of this invention are treated with saturated ammonia in methanol, which selectively replaces the bromine group with an amino group yielding the target amino substituted compound as illustrated below:

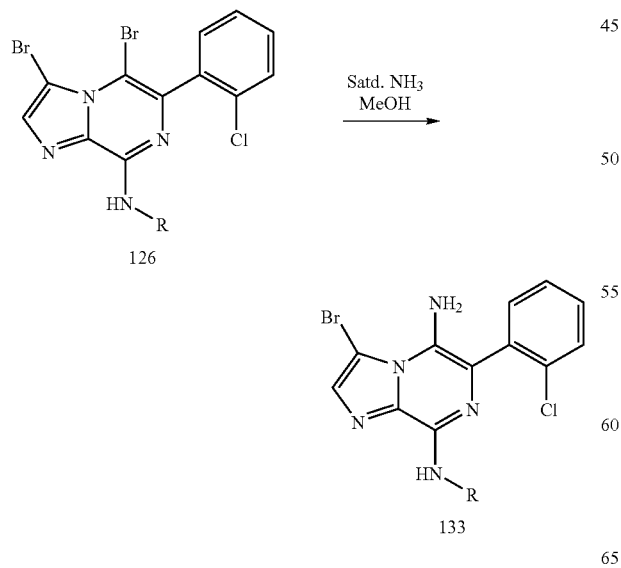

Some representative examples are illustrated in column 2 of Table 5 below:

TABLE 5

| Examples | Column 2 |
|---|---|
| 21 | |
| 22 | |
| 23 | |
| 24 | |
| 25 | |

TABLE 5-continued

| Examples | Column 2 |
|---|---|
| 26 | 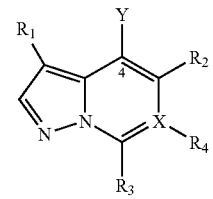 |
| 27 | |

ASSAY: The assay on the compounds of the present invention may be performed as follows.

BACULOVIRUS CONSTRUCTIONS: Cyclin E is cloned into pVL1393 (Pharmingen, La Jolla, Calif.) by PCR, with the addition of 5 histidine residues at the amino-terminal end to allow purification on nickel resin. The expressed protein is approximately 45 kDa. CDK2 is cloned into pVL1393 by PCR, with the addition of a haemaglutinin epitope tag at the carboxy-terminal end (YDVPDYAS). The expressed protein is approximately 34 kDa in size.

ENZYME PRODUCTION: Recombinant baculoviruses expressing cyclin E and CDK2 are co-infected into SF9 cells at an equal multiplicity of infection (MOI=5), for 48 hrs. Cells are harvested by centrifugation at 1000 RPM for 10 minutes, then pellets lysed on ice for 30 minutes in five times the pellet volume of lysis buffer containing 50 mM Tris pH 8.0, 150 mM NaCl, 1% NP40, 1 mM DTT and protease inhibitors (Roche Diagnostics GmbH, Mannheim, Germany). Lysates are spun down at 15000 RPM for 10 minutes and the supernatant retained. 5 ml of nickel beads (for one liter of SF9 cells) are washed three times in lysis buffer (Qiagen GmbH, Germany). Imidazole is added to the baculovirus supernatant to a final concentration of 20 mM, then incubated with the nickel beads for 45 minutes at 4° C. Proteins are eluted with lysis buffer containing 250 mM imidazole. Eluate is dialyzed overnight in 2 liters of kinase buffer containing 50 mM Tris pH 8.0, 1 mM DTT, 10 mM MgCl2, 100 uM sodium orthovanadate and 20% glycerol. Enzyme is stored in aliquots at −70° C.

IN VITRO KINASE ASSAY: Cyclin E/CDK2 kinase assays are performed in low protein binding 96-well plates (Corning Inc, Corning, N.Y.). Enzyme is diluted to a final concentration of 50 □g/ml in kinase buffer containing 50 mM Tris pH 8.0, 10 mM MgCl$_2$, mM DTT, and 0.1 mM sodium orthovanadate. The substrate used in these reactions is a biotinylated peptide derived from Histone H1 (from Amersham, UK). The substrate is thawed on ice and diluted to 2 μM in kinase buffer. Compounds are diluted in 10% DMSO to desirable concentrations. For each kinase reaction, 20 μl of the 50 μg/ml enzyme solution (1 μg of enzyme) and 20 μl of the 2 μM substrate solution are mixed, then combined with 10 μl of diluted compound in each well for testing. The kinase reaction is started by addition of 50 μl of 2 μM ATP and 0.1 μCi of 33P-ATP (from Amersham, UK). The reaction is allowed to run for 1 hour at room temperature. The reaction is stopped by adding 200 μl of stop buffer containing 0.1% Triton X-100, 1 mM ATP, 5 mM EDTA, and 5 mg/ml streptavidin coated SPA beads (from Amersham, UK) for 15 minutes. The SPA beads are then captured onto a 96-well GF/B filter plate (Packard/Perkin Elmer Life Sciences) using a Filtermate universal harvester (Packard/Perkin Elmer Life Sciences). Non-specific signals are eliminated by washing the beads twice with 2M NaCl then twice with 2 M NaCl with 1% phosphoric acid. The radioactive signal is then measured using a TopCount 96 well liquid scintillation counter (from Packard/Perkin Elmer Life Sciences).

IC$_{50}$ DETERMINATION: Dose-response curves are be plotted from inhibition data generated, each in duplicate, from 8 point serial dilutions of inhibitory compounds. Concentration of compound is plotted against % kinase activity, calculated by CPM of treated samples divided by CPM of untreated samples. To generate IC$_{50}$ values, the dose-response curves are then fitted to a standard sigmoidal curve and IC$_{50}$ values are derived by nonlinear regression analysis.

While the present invention has been described with in conjunction with the specific embodiments set forth above, many alternatives, modifications and other variations thereof will be apparent to those of ordinary skill in the art. All such alternatives, modifications and variations are intended to fall within the spirit and scope of the present invention.

What is claimed is:

1. A compound represented by the structural formula:

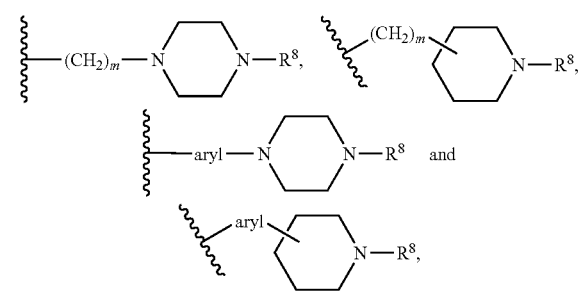

wherein:

X is C;

Y is selected from the group consisting of CN, NH$_2$, and CH$_2$NH$_2$;

R$^1$ is selected from the group consisting of H, halogen, R$^9$, NH$_2$CN, alkyl, alkenyl, alkynyl, aryl, heteroaryl, CF$_3$, heterocyclylalkyl, arylalkyl, heteroarylalkyl, heterocycloalkylalkyl, cycloalkyl, cycloalkylalkyl, C(O)OR$^4$, alkyl substituted with 1-6 R$^9$ groups which can be the same or different and are independently selected from the list of R$^9$ shown later below, wherein the aryl in the above-noted definitions for R$^1$ can be unsubstituted or optionally substituted with one or more moieties which can be the same or different, each moiety being independently selected from the group consisting of halogen, CN, NH$_2$, —OR$^5$, SR$^5$, —CH$_2$OR$^5$, —C(O)R$^5$, —SO$_3$H, —S(O₂)R⁶, —S(O₂)NR⁵R⁶, —NR⁵R⁶, —C(O)NR⁵R⁶, —CF₃, and —OCF₃;

R² is aryl, or heteroaryl wherein each of said aryl or heteroaryl for R² can be unsubstituted or optionally independently substituted with one or more moieties which can be the same or different, each moiety being independently selected from the group consisting of halogen, alkyl, alkenyl, alkynyl, aryl, cycloalkyl, CF₃, CN, —OCF₃, —(CR⁴R⁵)ₙOR⁵, —OR⁵, —R⁵OR⁵, —NR⁵R⁶, —(CR⁴R⁵)ₙNR⁵R⁶, —C(O₂)R⁵, —C(O)R⁵, —C(O)NR⁵R⁶, —SR⁶, —S(O₂)R⁶, —S(O₂)NR⁵R⁶, —N(R⁵)S(O₂)R⁷, —N(R⁵)C(O)R⁷, and —N(R⁵)C(O)NR⁵R⁶;

R₃ is selected from the group consisting of a halogen, amino, alkylamino, cycloalkylamino, arylalkylamino, heteroarylalkylamino, hydroxyalkylamino, heterocycloalkylalkylamino, wherein each of said amino, alkylamino, cycloalkylamino, arylalkylamino, heteroarylalkylamino, hydroxyalkylamino, and heterocycloalkylalkylamino can be unsubstituted or optionally independently substituted with one or more moieties, which can be the same or different, each moiety being independently selected from the group consisting of halogen, alkyl, aryl, heteroaryl, cycloalkyl, heterocycloalkyl, heteroarylalkyl, heterocycloalkylalkyl, cycloalkylalkyl, CF₃, OCF₃, CN, —OR⁵, —NR⁵R⁶, —C(R⁴R⁵)ₙOR⁵, —C(O₂)R⁵, —C(O)R⁵, —C(O)NR⁵R⁶, —SR⁶, —S(O₂)R⁷, —S(O₂)NR⁵R⁶, —N(R⁵)S(O₂)R⁷, —N(R⁵)C(O)R⁷ and —N(R⁵)C(O)NR⁵R⁶;

R⁴ is H, halogen, CN or alkyl;

R⁵ is H or alkyl;

R⁶ is selected from the group consisting of H, alkyl, aryl, arylalkyl, cycloalkyl, heterocycloalkyl, heteroaryl, and heteroarylalkyl, wherein each of said alkyl, aryl, arylalkyl, cycloalkyl, heterocycloalkyl, heteroaryl, and heteroarylalkyl can be unsubstituted or optionally substituted with one or more moieties which can be the same or different, each moiety being independently selected from the group consisting of halogen, alkyl, aryl, cycloalkyl, CF₃, OCF₃, CN, —OR⁵, —NR⁵R¹⁰, —N(R⁵)Boc, —(CR⁴R⁵)ₙOR⁵, —C(O₂)R⁵, —C(O)R⁵, —C(O)NR⁵R¹⁰, —SO₃H, —SR¹⁰, —S(O₂)R⁷, —S(O₂)NR⁵R¹⁰, —N(R⁵)S(O₂)R⁷, —N(R⁵)C(O)R⁷ and —N(R⁵)C(O)NR⁵R¹⁰;

R¹⁰ is selected from the group consisting a H, alkyl, aryl, arylalkyl, cycloalkyl, heterocycloalkyl, heteroaryl, and heteroarylalkyl, wherein each of said alkyl, aryl, arylalkyl, cycloalkyl, heterocycloalkyl, heterocycloalkyl, and heteroarylalkyl can be unsubstituted or optionally substituted with one or more moieties which can be the same or different, each moiety being independently selected from the group consisting of halogen, alkyl, aryl, cycloalkyl, CF₃, OCF₃, CN, —OR⁵, —NR⁴R⁵, —N(R⁵)Boc, —(CR⁴R⁵)ₙOR⁵, —C(O₂)R⁵, —C(O)NR⁴R⁵, —C(O)R⁵, —SO₃H, —SR⁵, —S(O₂)R⁷, —S(O₂)NR⁴R⁵, —N(R⁵)S(O₂)R⁷, —N(R⁵)C(O)R⁷ and —N(R⁵)C(O)NR⁴R⁵; optionally (i) R⁵ and R¹⁰ in the moiety —NR⁵R¹⁰, or (ii) R⁵ and R⁶ in the moiety —NR⁵R⁶, may be joined together to form a cycloalkyl or heterocycloalkyl moiety, with each of said cycloalkyl or heterocycloalkyl moiety being unsubstituted or optionally independently being substituted with one or more R⁹ groups;

R⁷ is selected from the group consisting of alkyl, cycloalkyl, aryl, heterocycloalkyl, heteroaryl, arylalkyl and heteroarylalkyl, wherein each of said alkyl, cycloalkyl, aryl, heterocycloalkyl, heteroaryl, arylalkyl and heteroarylalkyl, for R⁷ can be unsubstituted or optionally independently substituted with one or more moieties which can be the same or different, each moiety being independently selected from the group consisting of halogen, alkyl, aryl, cycloalkyl, CF₃, OCF₃, CN, —OR⁵, —NR⁵R¹⁰, —CH₂OR⁵, —C(O₂)R⁵, —C(O)NR⁵R¹⁰, —C(O)R⁵, —SR¹⁰, —S(O₂)R¹⁰, —S(O₂)NR⁵R¹⁰, —N(R⁵)S(O₂)R¹⁰, —N(R⁵)C(O)R¹⁰ and —N(R⁵)C(O)NR⁵R¹⁰;

R⁸ is selected from the group consisting of R⁶, —C(O)NR⁵R¹⁰, —CH₂OR⁴, —C(O)OR⁶, —C(O)R⁷ and —S(O₂)R⁷;

R⁹ is selected from the group consisting of halogen, —CN, —NR⁵R⁶, —(CH₂)ₙOR⁴, —C(O₂)R⁶, —C(O)NR⁵R⁶, —OR⁶, —SR⁶, —S(O₂)R⁷, —S(O₂)NR⁵R⁶, —N(R⁵)S(O₂)R⁷, —N(R⁵)C(O)R⁷ and —N(R⁵)C(O)NR⁵R⁶;

m is 0 to 4; and n is 1 to 4 or pharmaceutically acceptable salt there of.

2. The compound of claim 1, wherein R¹ is F, Cl, Br, CF₃, CN, lower alkyl, cycloalkyl or —(CH₂)ₙOR⁶.

3. The compound of claim 1, wherein R² is aryl or heteroaryl; wherein the aryl or heteroaryl moieties are unsubstituted or optionally independently substituted with one or more moieties which can be the same or different, each moiety being independently selected from the group consisting of halogen, CF₃, lower alkyl, —OCH₃, —CH₂OH, —CH₂CH₂OH, and CN.

4. The compound of claim 1, wherein R⁴ is H or CN.

5. The compound of claim 1, wherein R³ is selected from the group consisting of (pyridin-3-ylmethyl)-amino, (pyridin-2-ylmethyl)-amino, (pyridin-4-ylmethyl)-amino, isopropylamino, Benzylamino, 2-amino-ethanol and 1-amino-ethanol.

6. The compound of claim 1, wherein Y is selected from the group consisting of CN, NH₂, and CH₂NH₂.

7. The compound of claim 1, wherein Y is CN.

8. The compound of claim 1, wherein Y is NH₂.

9. The compound of claim 1, wherein Y is CH₂NH₂.

10. The compound of claim 1, wherein R³ is (pyridin-3-ylmethyl)-amino.

11. The compound of claim 1, wherein R³ is (pyridin-2-ylmethyl)-amino.

12. The compound of claim 1, wherein R³ is (pyridin-4-ylmethyl)-amino.

13. The compound of claim 2, wherein said R¹ is Br or Cl.

14. The compound of claim 2, wherein R¹ is isopropyl or ethyl.

15. The compound of claim 2, wherein R¹ is —CH₂OH or —CH₂OCH₃.

16. The compound of claim 2, wherein R¹ is CN.

17. The compound of claim 1, wherein R² is aryl.

18. The compound of claim 17, wherein R² is unsubstituted phenyl or phenyl substituted with one or more moieties selected from the group consisting of F, Br, Cl, OMe, CH₃ and CF₃.

19. A compound selected from the group consisting of:

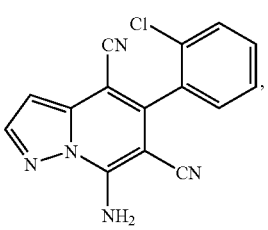 , 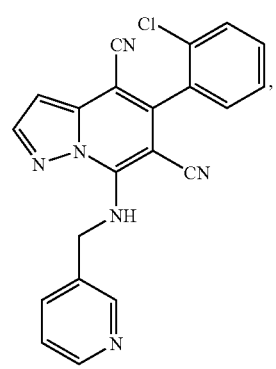 ,

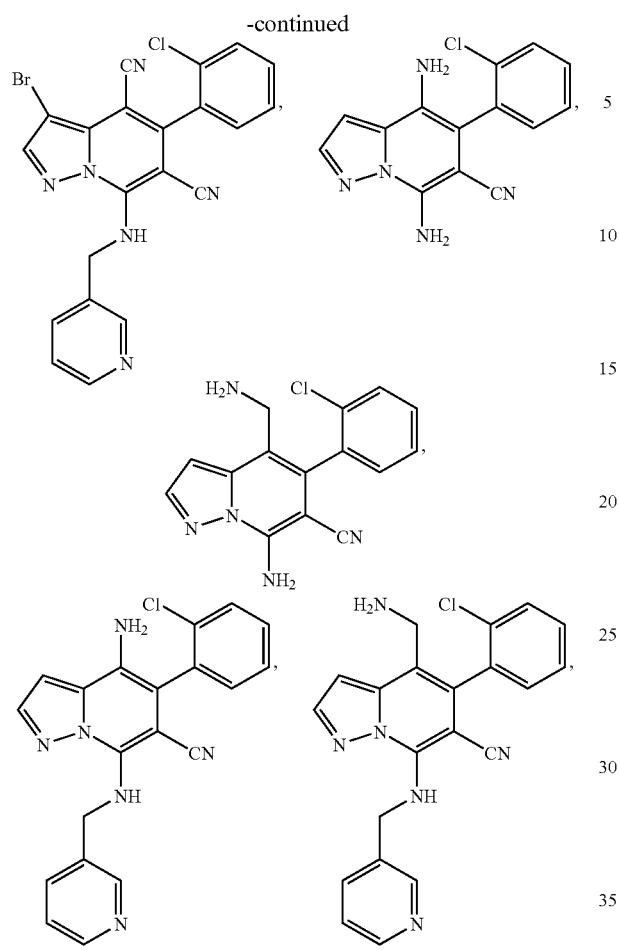
or a pharmaceutically acceptable salt thereof.
20. A compound of claim 1 in isolated and purified form.
* * * * *